US010251937B2

(12) United States Patent
Gaudriault et al.

(10) Patent No.: US 10,251,937 B2
(45) Date of Patent: Apr. 9, 2019

(54) RETRO-INVERSO ANALOGS OF SPADIN DISPLAY INCREASED ANTIDEPRESSANT EFFECTS

(71) Applicants: MEDINCELL, Jacou (FR); CENTRE NATIONAL DE LA RECHERCHE SCIENTIFIQUE, Paris (FR)

(72) Inventors: Georges Gaudriault, Montpellier (FR); Catherine Heurteaux, La Colle sur Loup (FR); Jean Mazella, Biot (FR); Marc Borsotto, Grasse (FR); Hamid Moha Ou Maati, Montpellier (FR); Julie Veyssiere, Clermont-Ferrand (FR)

(73) Assignees: MEDINCELL, Jacou (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/114,241

(22) PCT Filed: Jan. 27, 2015

(86) PCT No.: PCT/IB2015/000338
§ 371 (c)(1),
(2) Date: Jul. 26, 2016

(87) PCT Pub. No.: WO2015/110915
PCT Pub. Date: Jul. 30, 2015

(65) Prior Publication Data
US 2017/0072013 A1    Mar. 16, 2017

Related U.S. Application Data

(60) Provisional application No. 61/931,954, filed on Jan. 27, 2014.

(51) Int. Cl.
| | |
|---|---|
| *A61K 38/08* | (2006.01) |
| *A61K 38/10* | (2006.01) |
| *A61K 38/17* | (2006.01) |
| *A61K 47/60* | (2017.01) |

(52) U.S. Cl.
CPC .......... *A61K 38/1787* (2013.01); *A61K 38/08* (2013.01); *A61K 38/10* (2013.01); *A61K 38/17* (2013.01); *A61K 47/60* (2017.08)

(58) Field of Classification Search
CPC ........ A61K 47/60; A61K 38/17; A61K 38/08; A61K 38/10; A61K 38/1787
See application file for complete search history.

(56) References Cited

U.S. PATENT DOCUMENTS

| | | | | |
|---|---|---|---|---|
| 8,252,748 B2* | 8/2012 | Mazella | ............... | C07K 14/723 435/320.1 |
| 2005/0272652 A1* | 12/2005 | Gault | ................... | C07K 14/575 514/6.9 |
| 2012/0322060 A1 | 12/2012 | Mazella et al. | .............. | 435/6.11 |

FOREIGN PATENT DOCUMENTS

| | | | | |
|---|---|---|---|---|
| EP | 2077278 A1 | 7/2009 | ........... | C07K 14/705 |
| WO | WO 2004/056385 A2 | 7/2004 | ............ | A61K 38/00 |
| WO | WO 2009/132656 A2 | 11/2009 | ........... | C07K 14/705 |
| WO | WO 2014/001904 A1 | 1/2014 | ............. | A61K 47/37 |

OTHER PUBLICATIONS

Chorev et al. Partially modified retro-inverso-enkephalinamides: topochemical long-acting analogs in vitro and in vivo. Science. Jun. 15, 1979;204(4398):1210-2.*
International Search Report from corresponding International Patent Application No. PCT/IB2015/000338, dated Sep. 28, 2015.
Written Opinion of the International Searching Authority PCT/IB2015/000338, dated Sep. 28, 2015.
Westergaard et al., "Functional Organization of the Sortilin Vps10p Domain," Journal of Biological Chemistry, American Society for Biochemistry and Molecular Biology, vol. 279, No. 48, Nov. 26, 2004, pp. 50221-50229.
Mazella et al., "Spadin, a Sortilin-Derived Peptide, Targeting Rodent TREK-1 Channels: A New Concept in the Antidepressant Drug Design," PLoS Biology, vol. 8, No. 4, Apr. 13, 2010, p. e1000355.
Veyssiere et al., "Retroinverso Analogs of Spadin Display Increased Antidepressant Effects," Psychopharmacology, vol. 232, No. 3, Aug. 2, 2014, pp. 561-574.
Maati et al., "Spadin as a New Antidepressant: Absence of TREK-1 Related Side Effects," Neuropharmacology, Pergamon Press, vol. 62, No. 1, Jul. 13, 2011, pp. 273-288.

* cited by examiner

*Primary Examiner* — Gregory S Emch
(74) *Attorney, Agent, or Firm* — Kusner & Jaffe

(57) ABSTRACT

Compositions, pharmaceutical compositions and biodegradable pharmaceutical compositions containing at least one analog of spadin or at least one analog of a propeptides of spadin or mixtures thereof are described. Methods for treating depression using the analogs of spadin or analogs of propeptides of spadin or mixtures thereof, as well as methods for blocking TREK-1 channel activity are also disclosed.

5 Claims, 18 Drawing Sheets
Specification includes a Sequence Listing.

| SEQ ID N° | Sequence |
|---|---|
| 1 | APLPRWSGPIGVSWGLR |
| 2 | QDRLDAPPPPAAPLPRWSGPIGVSWGLRAAAAGGAFPRGGRWRR |
|  | YAPLPRWSGPIGVSWGLR |
| 3 | Ac-APLPRWSGPIGVSWGLR-NH2 |
| 4 | Ac-rlGwsvGipGswrplpa-NH2 |
| 5 | Ac-GVSWGLR-NH2 |
| 6 | Ac-IGVSWGLR-NH2 |
| 7 | Ac-rlGwsvGi-NH2 |
| 8 | Ac-QDRLDAPPPPAAPLPRWSGPIGVSWGLR-NH2 |
| 9 | Ac-rlGwsvGipGswrplpaappppadlrdq-NH2 |
| 10 | Ac-APPPPAAPLPRWSGPIGVSWGLR-NH2 |
| 11 | Ac-rlGwsvGipGswrplpaappppa-NH2 |
| 12 | Ac-QDRLDAPPPPAAPLPRWSGPIGVSWGLRAAAAGGAFPRGGRWRR-NH2 |
| 13 | Ac-rrwrGGrpfaGGaaaarlGwsvGipGswrplpaappppadlrdq-NH2 |
| 14 | Ac-APLPRWSAPIAVSWALR-NH2 |
| 15 | Ac-rlawsvaipaswrplpa-NH2 |
| 16 | Ac-PPLLRWAGPVGVSWGLR-NH2 |
| 17 | Ac-rlGwsvGvpGawrllpp-NH2 |
| 18 | Ac-APLSRWPGPVGVSWGLR-NH2 |
| 19 | Ac-rlGwsvGvpGpwrslpa-NH2 |
| 20 | ⌐rlGwsvGipGswrplpa¬ |
| 21 | ⌐rlGwsvGipGswrplparlGwsvGipGswrplpa¬ |
| 22 | ⌐rlawsvaipaswrplpa¬ |
| 23 | ⌐rlawsvaipaswrplparlawsvaipaswrplpa¬ |

FIGURE 1

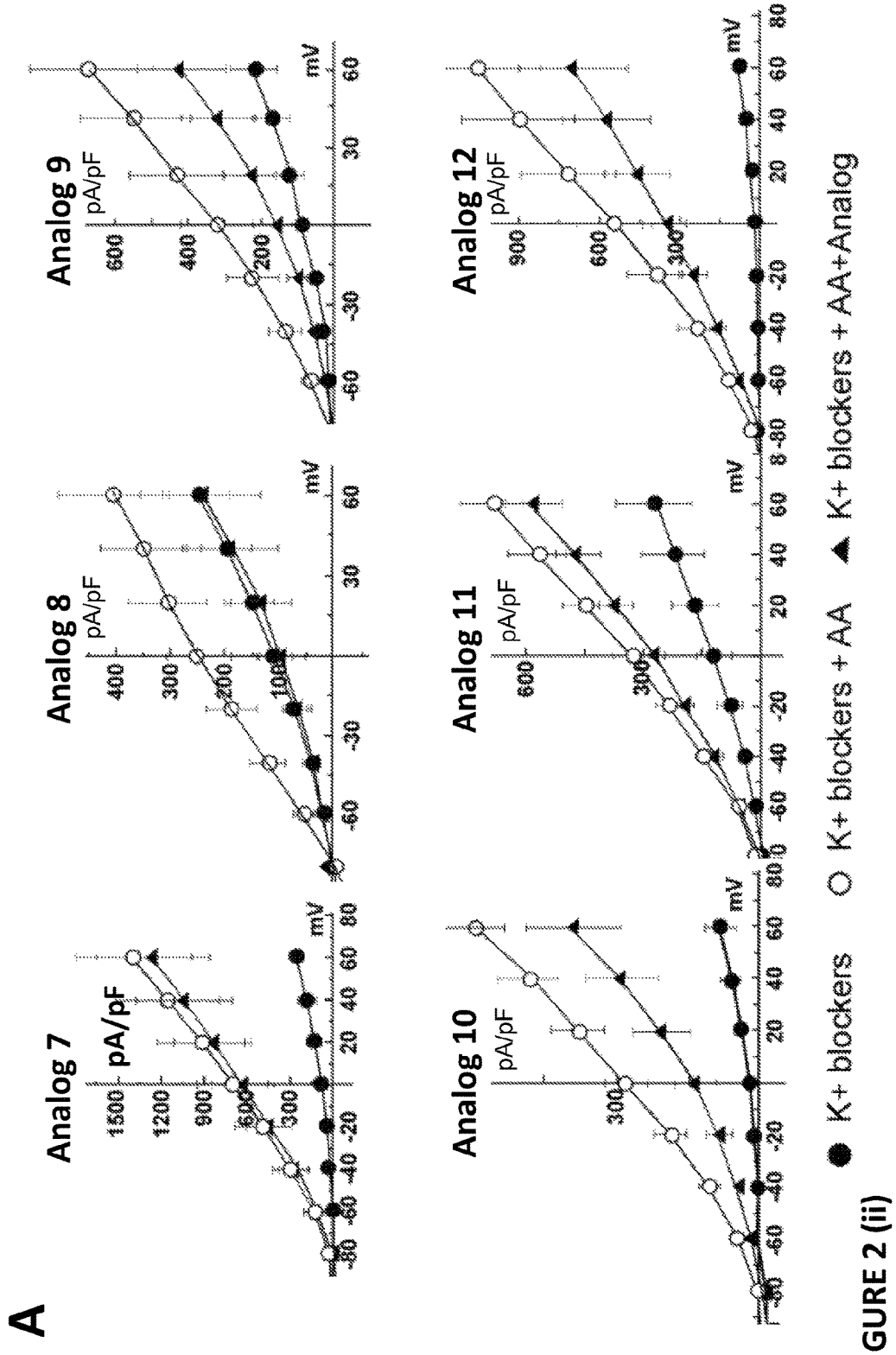
FIGURE 2 (ii)

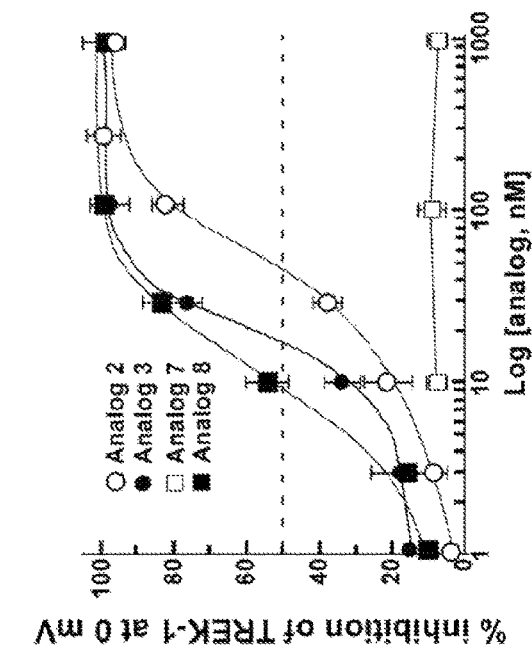
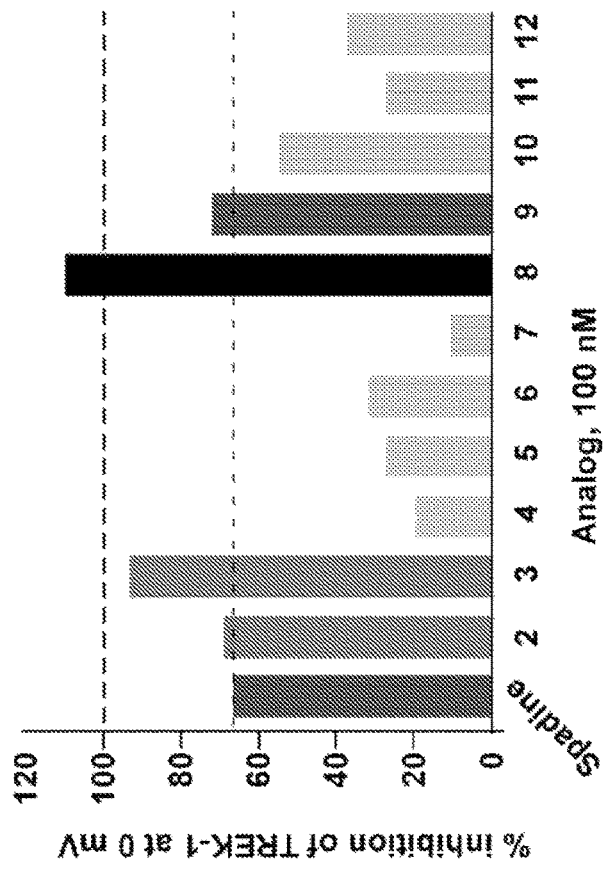
FIGURE 2(iii)

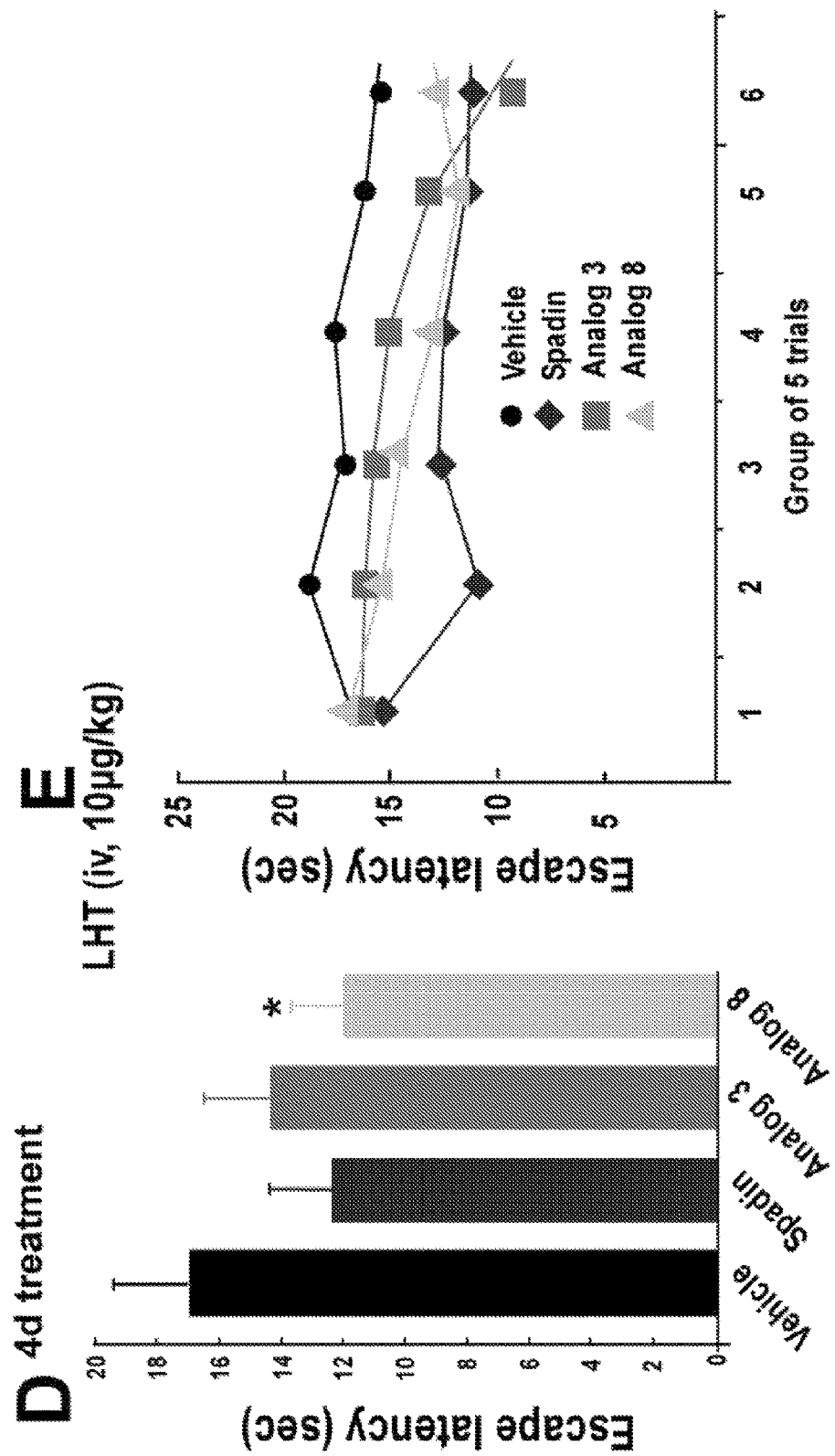
FIGURE 3 (ii)

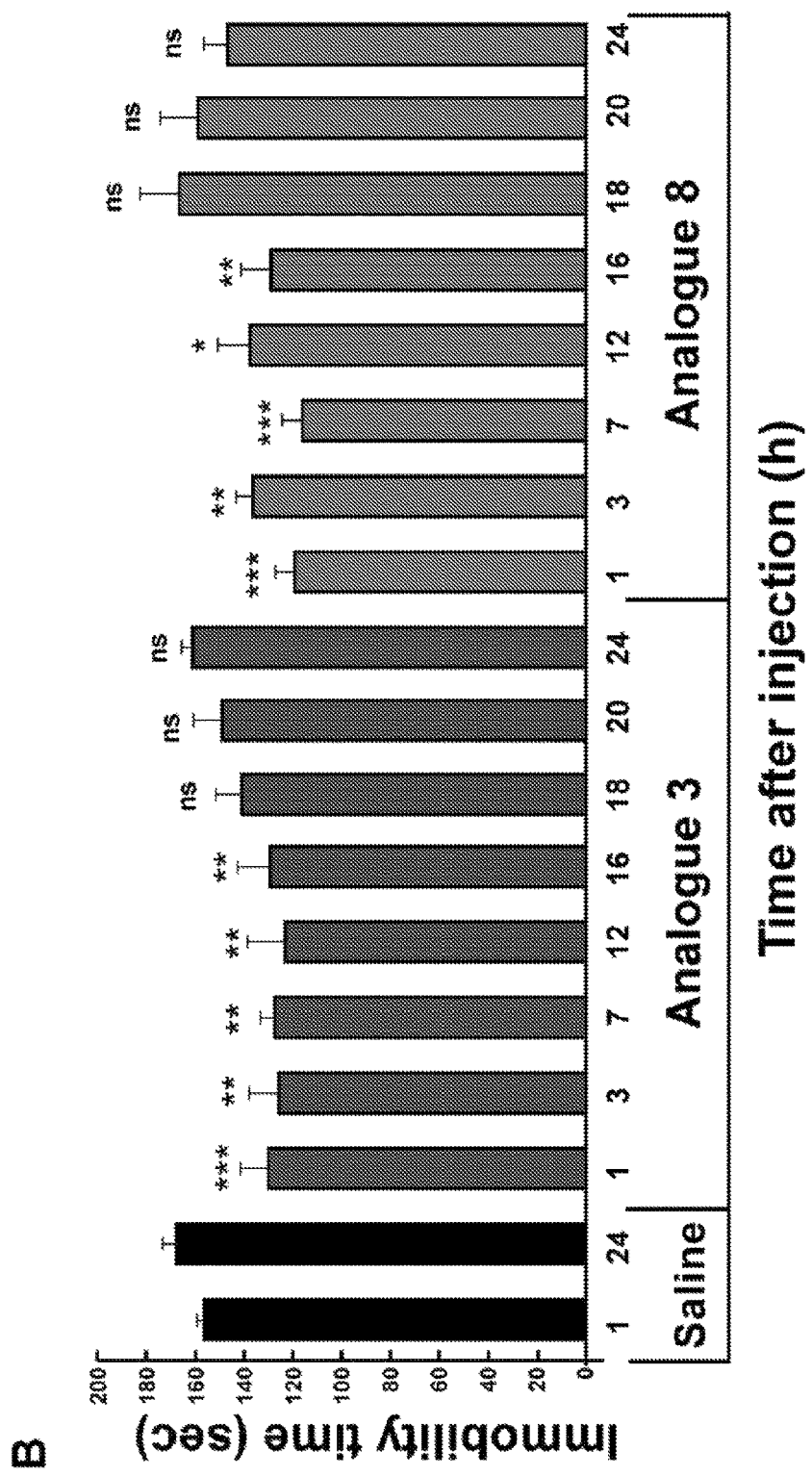
FIGURE 4 (ii)

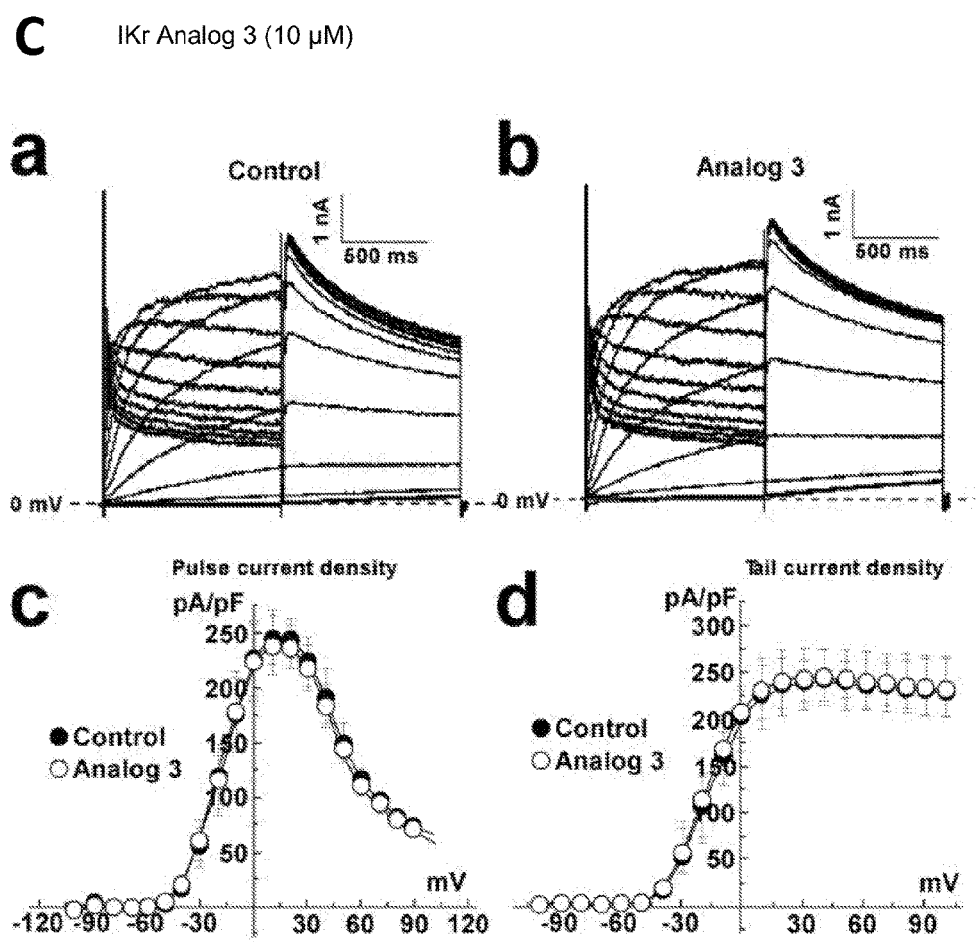
FIGURE 6 (ii)

D IKs
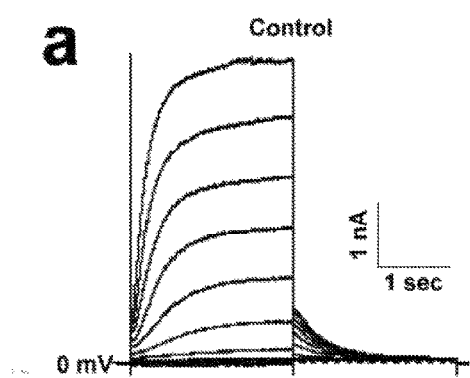
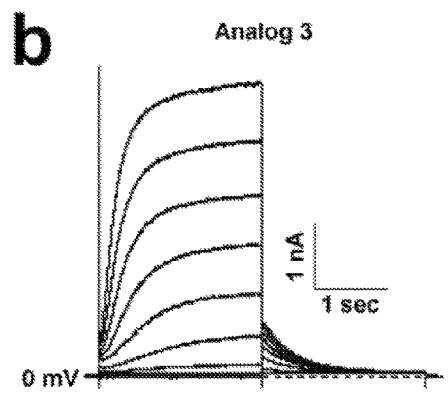
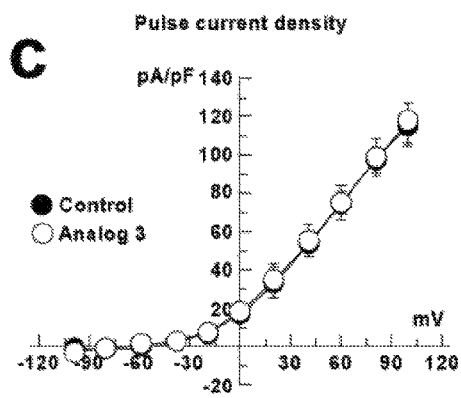
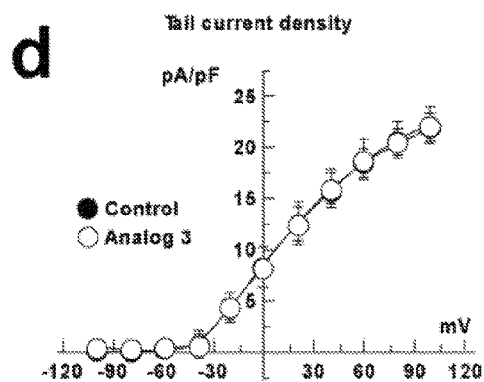
FIGURE 6(iii)

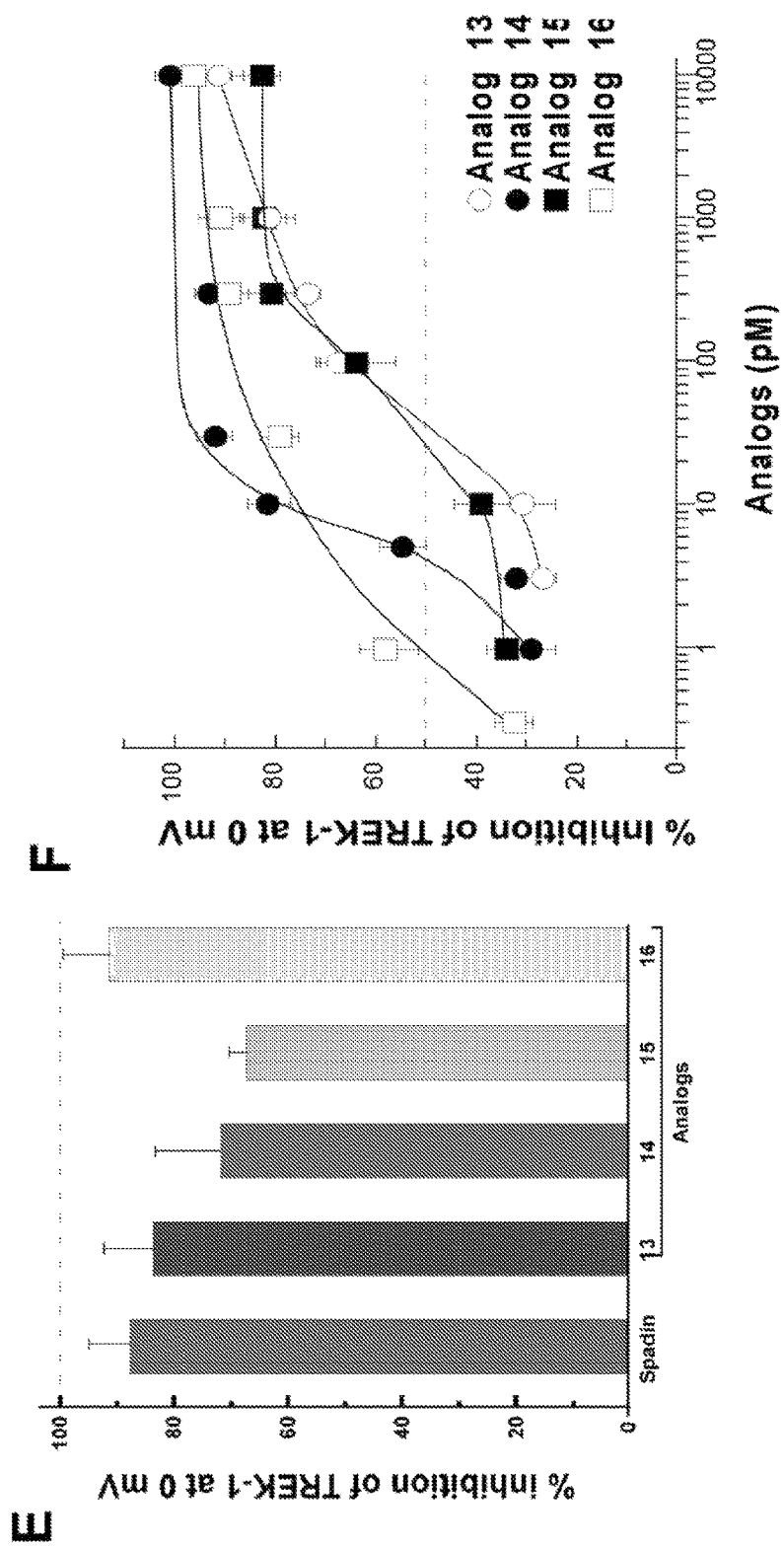
FIGURE 8 (ii)

SEQUENCE LISTING

```
<160> NUMBER OF SEQ ID NOS: 23

<210> SEQ ID NO 1
<211> LENGTH: 17
<212> TYPE: PRT
<213> ORGANISM: Artificial Sequence
<220> FEATURE:
<223> OTHER INFORMATION: Synthetic - spadin peptide analog
<220> FEATURE:
<221> NAME/KEY: PEPTIDE
<222> LOCATION: (1)..(17)

<400> SEQUENCE: 1

Ala Pro Leu Pro Arg Trp Ser Gly Pro Ile Gly Val Ser Trp Gly Leu
1               5                   10                  15
Arg

<210> SEQ ID NO 2
<211> LENGTH: 44
<212> TYPE: PRT
<213> ORGANISM: Artificial Sequence
<220> FEATURE:
<223> OTHER INFORMATION: Synthetic - spadin propeptide
<220> FEATURE:
<221> NAME/KEY: PEPTIDE
<222> LOCATION: (1)..(44)

<400> SEQUENCE: 2

Gln Asp Arg Leu Asp Ala Pro Pro Pro Ala Ala Pro Leu Pro Arg
```

```
                1               5                  10                 15
Trp Ser Gly Pro Ile Gly Val Ser Trp Gly Leu Arg Ala Ala Ala Ala
                20                 25                 30
Gly Gly Ala Phe Pro Arg Gly Gly Arg Trp Arg Arg
        35                 40

<210> SEQ ID NO 3
<211> LENGTH: 17
<212> TYPE: PRT
<213> ORGANISM: Artificial Sequence
<220> FEATURE:
<223> OTHER INFORMATION: Synthetic - spadin peptide analog
<220> FEATURE:
<221> NAME/KEY: PEPTIDE
<222> LOCATION: (1)..(17)

<400> SEQUENCE: 3

Ala Pro Leu Pro Arg Trp Ser Gly Pro Ile Gly Val Ser Trp Gly Leu
1               5                   10                  15

Arg

<210> SEQ ID NO 4
<211> LENGTH: 17
<212> TYPE: PRT
<213> ORGANISM: Artificial Sequence
<220> FEATURE:
<223> OTHER INFORMATION: Retro-inverso peptide

<400> SEQUENCE: 4

Arg Leu Gly Trp Ser Val Gly Ile Pro Gly Ser Trp Arg Pro Leu Pro
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: Synthetic - spadin peptide analog
<220> FEATURE:
<221> NAME/KEY: PEPTIDE
<222> LOCATION: (1)..(7)

<400> SEQUENCE: 5

Gly Val Ser Trp Gly Leu Arg
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic - Spadin peptide analog
<220> FEATURE:
<221> NAME/KEY: PEPTIDE
<222> LOCATION: (1)..(8)

<400> SEQUENCE: 6

Ile Gly Val Ser Trp Gly Leu Arg
1               5

<210> SEQ ID NO 7
<211> LENGTH: 8
<212> TYPE: PRT
<213> ORGANISM: Artificial Sequence
<220> FEATURE:
```

```
<223> OTHER INFORMATION: Retro-inverso peptide

<400> SEQUENCE: 7

Arg Leu Gly Trp Ser Val Gly Ile
1               5

<210> SEQ ID NO 8
<211> LENGTH: 28
<212> TYPE: PRT
<213> ORGANISM: Artificial Sequence
<220> FEATURE:
<223> OTHER INFORMATION: Synthetic - Spadin peptide analog
<220> FEATURE:
<221> NAME/KEY: PEPTIDE
<222> LOCATION: (1)..(28)

<400> SEQUENCE: 8

Gln Asp Arg Leu Asp Ala Pro Pro Pro Ala Ala Pro Leu Pro Arg
1               5                   10                  15

Trp Ser Gly Pro Ile Gly Val Ser Trp Gly Leu Arg
            20                  25

<210> SEQ ID NO 9
<211> LENGTH: 28
<212> TYPE: PRT
<213> ORGANISM: Artificial Sequence
<220> FEATURE:
<223> OTHER INFORMATION: Retro-inverso peptide

<400> SEQUENCE: 9

Arg Leu Gly Trp Ser Val Gly Ile Pro Gly Ser Trp Arg Pro Leu Pro
1               5                   10                  15

Ala Ala Pro Pro Pro Pro Ala Asp Leu Arg Asp Gln
            20                  25

<210> SEQ ID NO 10
<211> LENGTH: 23
<212> TYPE: PRT
<213> ORGANISM: Artificial Sequence
<220> FEATURE:
<223> OTHER INFORMATION: Synthetic - Spadin peptide analog
<220> FEATURE:
<221> NAME/KEY: PEPTIDE
<222> LOCATION: (1)..(23)

<400> SEQUENCE: 10

Ala Pro Pro Pro Pro Ala Ala Pro Leu Pro Arg Trp Ser Gly Pro Ile
1               5                   10                  15

Gly Val Ser Trp Gly Leu Arg
            20

<210> SEQ ID NO 11
<211> LENGTH: 23
<212> TYPE: PRT
<213> ORGANISM: Artificial Sequence
<220> FEATURE:
<223> OTHER INFORMATION: Retro-inverso peptide

<400> SEQUENCE: 11

Arg Leu Gly Trp Ser Val Gly Ile Pro Gly Ser Trp Arg Pro Leu Pro
1               5                   10                  15

Ala Ala Pro Pro Pro Pro Ala
            20

<210> SEQ ID NO 12
```

```
<211> LENGTH: 44
<212> TYPE: PRT
<213> ORGANISM: Artificial Sequence
<220> FEATURE:
<223> OTHER INFORMATION: Synthetic - spadin peptide analog
<220> FEATURE:
<221> NAME/KEY: PEPTIDE
<222> LOCATION: (1)..(44)

<400> SEQUENCE: 12

Gln Asp Arg Leu Asp Ala Pro Pro Pro Ala Ala Pro Leu Pro Arg
1               5                   10                  15

Trp Ser Gly Pro Ile Gly Val Ser Trp Gly Leu Arg Ala Ala Ala
                20                  25                  30

Gly Gly Ala Phe Pro Arg Gly Gly Arg Trp Arg Arg
            35                  40

<210> SEQ ID NO 13
<211> LENGTH: 44
<212> TYPE: PRT
<213> ORGANISM: Artificial Sequence
<220> FEATURE:
<223> OTHER INFORMATION: Retro-inverso peptide

<400> SEQUENCE: 13

Arg Arg Trp Arg Gly Gly Arg Pro Phe Ala Gly Gly Ala Ala Ala
1               5                   10                  15

Arg Leu Gly Trp Ser Val Gly Ile Pro Gly Ser Trp Arg Pro Leu Pro
                20                  25                  30

Ala Ala Pro Pro Pro Ala Asp Leu Arg Asp Gln
            35                  40

<210> SEQ ID NO 14
<211> LENGTH: 17
<212> TYPE: PRT
<213> ORGANISM: Artificial Sequence
<220> FEATURE:
<223> OTHER INFORMATION: Synthetic - spadin peptide analog
<220> FEATURE:
<221> NAME/KEY: PEPTIDE
<222> LOCATION: (1)..(17)

<400> SEQUENCE: 14

Ala Pro Leu Pro Arg Trp Ser Ala Pro Ile Ala Val Ser Trp Ala Leu
1               5                   10                  15

Arg

<210> SEQ ID NO 15
<211> LENGTH: 17
<212> TYPE: PRT
<213> ORGANISM: Artificial Sequence
<220> FEATURE:
<223> OTHER INFORMATION: Retro-inverso peptide

<400> SEQUENCE: 15

Arg Leu Ala Trp Ser Val Ala Ile Pro Ala Ser Trp Arg Pro Leu Pro
1               5                   10                  15

Ala

<210> SEQ ID NO 16
<211> LENGTH: 17
<212> TYPE: PRT
<213> ORGANISM: Artificial Sequence
<220> FEATURE:
<223> OTHER INFORMATION: Synthetic - spadin peptide analog
```

```
<220> FEATURE:
<221> NAME/KEY: PEPTIDE
<222> LOCATION: (1)..(17)

<400> SEQUENCE: 16

Pro Pro Leu Leu Arg Trp Ala Gly Pro Val Gly Val Ser Trp Gly Leu
1               5                   10                  15

Arg

<210> SEQ ID NO 17
<211> LENGTH: 17
<212> TYPE: PRT
<213> ORGANISM: Artificial Sequence
<220> FEATURE:
<223> OTHER INFORMATION: Retro-inverso peptide

<400> SEQUENCE: 17

Arg Leu Gly Trp Ser Val Gly Val Pro Gly Ala Trp Arg Leu Leu Pro
1               5                   10                  15

Pro

<210> SEQ ID NO 18
<211> LENGTH: 17
<212> TYPE: PRT
<213> ORGANISM: Artificial Sequence
<220> FEATURE:
<223> OTHER INFORMATION: Synthetic - Spadin peptide analog
<220> FEATURE:
<221> NAME/KEY: PEPTIDE
<222> LOCATION: (1)..(17)

<400> SEQUENCE: 18

Ala Pro Leu Ser Arg Trp Pro Gly Pro Val Gly Val Ser Trp Gly Leu
1               5                   10                  15

Arg

<210> SEQ ID NO 19
<211> LENGTH: 17
<212> TYPE: PRT
<213> ORGANISM: Artificial Sequence
<220> FEATURE:
<223> OTHER INFORMATION: Retro-inverso peptide

<400> SEQUENCE: 19

Arg Leu Gly Trp Ser Val Gly Val Pro Gly Pro Trp Arg Ser Leu Pro
1               5                   10                  15

Ala

<210> SEQ ID NO 20
<211> LENGTH: 17
<212> TYPE: PRT
<213> ORGANISM: Artificial Sequence
<220> FEATURE:
<223> OTHER INFORMATION: Synthetic - spadin peptide analog

<400> SEQUENCE: 20

Arg Leu Gly Trp Ser Val Gly Ile Pro Gly Ser Trp Arg Pro Leu Pro
1               5                   10                  15

Ala

<210> SEQ ID NO 21
<211> LENGTH: 34
<212> TYPE: PRT
<213> ORGANISM: Artificial Sequence
```

```
<220> FEATURE:
<223> OTHER INFORMATION: Synthetic - spadin peptide analog

<400> SEQUENCE: 21

Arg Leu Gly Trp Ser Val Gly Ile Pro Gly Ser Trp Arg Pro Leu Pro
1               5                   10                  15

Ala Arg Leu Gly Trp Ser Val Gly Ile Pro Gly Ser Trp Arg Pro Leu
            20                  25                  30

Pro Ala

<210> SEQ ID NO 22
<211> LENGTH: 17
<212> TYPE: PRT
<213> ORGANISM: Artificial Sequence
<220> FEATURE:
<223> OTHER INFORMATION: Synthetic - spadin peptide analog

<400> SEQUENCE: 22

Arg Leu Ala Trp Ser Val Ala Ile Pro Ala Ser Trp Arg Pro Leu Pro
1               5                   10                  15

Ala

<210> SEQ ID NO 23
<211> LENGTH: 34
<212> TYPE: PRT
<213> ORGANISM: Artificial Sequence
<220> FEATURE:
<223> OTHER INFORMATION: Synthetic - spadin peptide analog

<400> SEQUENCE: 23

Arg Leu Ala Trp Ser Val Ala Ile Pro Ala Ser Trp Arg Pro Leu Pro
1               5                   10                  15

Ala Arg Leu Ala Trp Ser Val Ala Ile Pro Ala Ser Trp Arg Pro Leu
            20                  25                  30

Pro Ala
```

RETRO-INVERSO ANALOGS OF SPADIN DISPLAY INCREASED ANTIDEPRESSANT EFFECTS

FIELD OF THE INVENTION

The present invention relates to compositions, pharmaceutical compositions and biodegradable pharmaceutical compositions containing at least one analog of spadin or at least one analog of a propeptide of spadin or mixtures thereof of said at least one analog. Methods for treating depression using the at least one analog of spadin or the at least one analog of a propeptide of spadin or mixtures thereof of said at least one analog, as well as methods for blocking TREK-1 channel activity are also disclosed.

BACKGROUND OF THE PRESENT INVENTION

Depression is a devastating neuropsychiatric disorder and affects approximately 20% of the population. Depression is predicted to be a major cause of morbidity worldwide in the next ten years and will induce an important economic burden (Greenberg, P. E. et al. The economic burden of depression in the United States: how did it change between 1990 and 2000? J Clin Psychiatry 64, 1465 (2003); Moussavi, S. et al. Depression, chronic diseases, and decrements in health: results from the World Health Surveys. Lancet 370, 851, (2007)). Depressions are multifactorial and multigenic diseases characterized by many symptoms like fatigue, anhedonia, pessimism, irritability, sleep troubles, increased or decreased appetite, guiltiness and suicidal tendencies. (Nestler, E. J. et al. Neurobiology of depression. Neuron 34, 13 (2002)). 60 years ago antidepressant treatments had been revolutionized by the discovery of tricyclic antidepressants and monoamine oxidase inhibitors. Later, a second generation of antidepressants was developed with the selective serotonin reuptake or norepinephrine selective reuptake inhibitors. Despite their efficacy, around one third of patients remain unresponsive to these drugs and antidepressants display some adverse side effects and have a long onset of action of at least 2 weeks (Sicouri, S. et al. Sudden cardiac death secondary to antidepressant and antipsychotic drugs. Expert Opin Drug Saf 7, 181, (2008)). Furthermore detecting and preventing depression is costly and is estimated to be about 53 billion dollars per year in the United States alone.

Besides depression in humans, animals including, for example, dogs, cats, horses, monkeys, rats, birds and the like also get depressed. Signs of depression in animals are revealed by their inactivity, changes in appetite, changes in sleep habits, becoming withdrawn or becoming inactive. Eli Lilly researched dog depression and found that 10.4 million dogs in the U.S. alone or 17% suffer from separation anxiety, a type of dog depression. When the drug Reconcile® (Prozac®) was administered to these animals, 73% of the dogs were less depressive as indicated by better behavior.

It was previously demonstrated that the inhibition of the potassium channel TREK-1 led to an antidepressant phenotype (Heurteaux, C. et al. Deletion of the background potassium channel TREK-1 results in a depression-resistant phenotype. Nat Neurosci 9, 1134, (2006)). TREK-1 channels belong to the family of potassium channels with a unique structure characterized by two pore domains and four transmembrane segments in each subunit (Ducroq, J. et al. Dexrazoxane protects the heart from acute doxorubicin-induced QT prolongation: a key role for I(Ks). Br J Pharmacol 159, 93, (2010)). The genes encoding these ion channels are called KCNK (Porsolt, R. D. et al. Depression: a new animal model sensitive to antidepressant treatments. Nature 266, 730, (1977)). It was demonstrated by Kennard et al (Santarelli, L. et al. Requirement of hippocampal neurogenesis for the behavioral effects of antidepressants. Science 301, 805, (2003)) that fluoxetine (Prozac®) and its active metabolite, norfluoxetine inhibit the human two-pore domain potassium channel TREK-1.

This led to the investigation for specific inhibitors of the TREK-1 channel (Mazella, J. et al. Spadin, A sortilin-derived peptide, targeting rodent TREK-1 channels: a new concept in the antidepressant drug design. PLoS Biol 8, e1000355, (2010)). that could be utilized as antidepressants without side effects on both cardiac function and TREK-1 controlled functions (Moha Ou Maati, H. et al. Spadin as a new antidepressant: absence of TREK-1-related side effects. Neuropharmacology 62, 278, (2012)). A peptide named spadin was discovered, which resulted from modification of the sortilin receptor (Mazella, J. et al. The 100-kDa neurotensin receptor is gp95/sortilin, a non-G-protein-coupled receptor. J Biol Chem 273, 26273, (1998)). Spadin is a 17 amino acid peptide which was designed from a 44 amino acid peptide (called PE, the propeptide of Spadin) released by furin in the late Golgi apparatus during the post-translational maturation of the sortilin receptor (Munck Petersen, C. et al. Propeptide cleavage conditions sortilin/neurotensin receptor-3 for ligand binding. Embo J 18, 595, (1999)). Spadin is able to block the TREK-1 potassium channel current and displays antidepressant effects in different behavioral tests (Mazella, J. et al. Spadin, a sortilin-derived peptide, targeting rodent TREK-1 channels: a new concept in the antidepressant drug design. PLoS Biol 8, e1000355, (2010)). Spadin leads to an in vivo increase in efficacy of 5-HT neurotransmission as evidenced by an increased firing activity of DRN-5-HT neurons.

Additionally, like other antidepressant drugs, spadin is also capable of increasing neurogenesis and serotoninergic transmission. Unlike most of the antidepressants used, which need 21 days to be efficient, spadin has a quicker onset of action since it is able to induce these improvements only after a 4 day treatment (Mazella, J. et al. Spadin, a sortilin-derived peptide, targeting rodent TREK-1 channels: a new concept in the antidepressant drug design. PLoS Biol 8, e1000355, (2010)). In the $K_{2P}$ potassium channel family, spadin is specific for TREK-1 channels (Moha Ou Maati, H. et al. Spadin as a new antidepressant: absence of TREK-1-related side effects. Neuropharmacology 62, 278, (2012)). Moreover, activation of TREK-1 channels was demonstrated to be of benefit in different functions such as general anesthesia, neuroprotection by the way of polyunsaturated fatty acids, pain, ischemia and epilepsy (Alloui, A. et al. TREK-1, a K+ channel involved in polymodal pain perception. Embo J 25, 2368, (2006); Heurteaux, C. et al. Alpha-linolenic acid and riluzole treatment confer cerebral protection and improve survival after focal brain ischemia. Neuroscience 137, 241, (2006); Lauritzen, I. et al. Polyunsaturated fatty acids are potent neuroprotectors. Embo J 19, 1784, (2000); Noel, J. et al. The mechano-activated K+ channels TRAAK and TREK-1 control both warm and cold perception. Embo J 28, 1308, (2009)). Nevertheless, blockade of TREK-1 channels by spadin did not interfere with these functions. In other words spadin is devoid of side effects related to TREK-1 functions (Moha Ou Maati, H. et al. Spadin as a new antidepressant: absence of TREK-1-related side effects. Neuropharmacology 62, 278, (2012)). Importantly, spadin induces no cardiac dysfunctions, systolic pressure and pulses were not affected by a three week spadin treatment and spadin was unable to block the two most important repolarizing currents in heart ($IK_R$, $IK_S$) (Moha Ou Maati, H. et al. Spadin as a new antidepressant: absence of TREK-1-related side effects. Neuropharmacology 62, 278, (2012)). Taken together these properties are evidence for considering spadin as a new antidepressant drug.

However, since taking antidepressive drugs involve long term treatments formulating spadin had to be taken into account. Daily dose formulations are usually not effective due to the fact that many patients are non-compliant with taking their medications each day. Furthermore, the bioavailability of spadin could be improved to make the peptide more resistant to protease hydrolysis.

Thus, it is an object of the present invention to find new targets for depression based on TREK-1 inhibition and to develop new molecules with antidepressant activity.

It is another object to find compositions for treating depression with improved bioavailability and very minute side effects.

It is yet another object to provide a pharmaceutical composition that is formulated for a long duration.

These and other objects are achieved by the present invention as evidenced by the summary of the invention, description of the preferred embodiments and the claims.

SUMMARY OF THE INVENTION

The present invention provides compositions comprising at least one analog of spadin or at least one analog of a propeptide of spadin or mixtures thereof of said at least one analog and an acceptable vehicle. The at least one analog of spadin or the at least one analog of a propeptide of spadin or mixtures thereof of said at least one analog can be a retro-inverso peptide or can be an end-capped peptide. When the at least one analog of spadin or the at least one analog of a propeptide of spadin is end-capped, it is end-capped with an acetylated N-terminus or an amidated C-terminus or an acetylated N-terminus and an amidated C-terminus.

In another aspect, compositions are provided, wherein the at least one analog of spadin or the at least one analog of a propeptide of spadin or mixtures thereof of said at least one analog is selected from the group of: Ac-APLPRWSGPIGVSWGLR-NH2 (SEQ ID NO:3), Ac-rlGwsvGipGswrplpa-NH$_2$ (SEQ ID NO:4), Ac-GVSWGLR-NH$_2$ (SEQ ID NO:5), Ac-IGVSWGLR-NH$_2$, (SEQ ID NO:6), Ac-rlGwsvGi-NH$_2$ (SEQ ID NO:7), Ac-QDRLAPPPPAAPLPRWSGPIGVSWGLR-NH$_2$ (SEQ ID NO:8), Ac-rlGwsvGipGswrplpaappppadlrdq-NH$_2$ (SEQ ID NO:9), Ac-APPPPAAPLPRWSGPIGVSWGLR-NH$_2$ (SEQ ID NO:10), Ac-rlGwsvGipGswrplpaappppa-NH$_2$ (SEQ ID NO:11), Ac-QDRLAPPPPAAPLPRWSGPIGVSWGL-RAAAAGGAFPRGGRWRR-NH$_2$ (SEQ ID NO:12), Ac-rrwrGGrpfaGGaaaarlGwsvGipGswrplpaappppadlrdq-NH$_2$ (SEQ ID NO:13), Ac-APLPRWSAPIAVSWALR-NH$_2$ (SEQ ID NO:14), Ac-rlawsvaipaswrplpa-NH$_2$ (SEQ ID NO: 15), c(rlGwsvGipGswrplpa) (SEQ ID NO:20), c(rlGwsvGipGswrplparlGwsvGipGswrplpa) (SEQ ID NO:21) and mixtures thereof.

A composition is provided wherein the at least one analog of spadin or the at least one analog of a propeptide of spadin or mixtures thereof of said at least one analog is Ac-rlGwsvGipGswrplpa-NH$_2$ (SEQ ID NO:4) or Ac-rlGwsvGipGswrplpaappppadlrdq-NH$_2$ (SEQ ID NO:9) or Ac-rlGwsvGipGswrplpa-NH$_2$ (SEQ ID NO:4) and Ac-rlGwsvGipGswrplpaappppadlrdq-NH$_2$ (SEQ ID NO:9) is yet another aspect of the invention.

The compositions, as described herein, contain acceptable vehicles such as distilled water, buffers, glycerol, polypropylene glycol, saline (NaCl 0.9%), phosphate buffered saline dextrose, ethanol and mixtures thereof.

In yet another aspect pharmaceutical compositions comprising at least one analog of spadin or at least one analog of a propeptide of spadin or mixtures thereof of said at least one analog and a pharmaceutically acceptable vehicle is provided. The at least one analog of spadin or the at least one analog of a propeptide of spadin can be a retro-inverso peptide or an end-capped peptide. When the at least one analog of spadin or the at least one analog of a propeptide of spadin is end-capped, it is end-capped with an acetylated N-terminus or an amidated C-terminus or an acetylated N-terminus and an amidated C-terminus.

In another aspect, pharmaceutical compositions are provided, wherein the at least one analog of spadin or the at least one analog of a propeptide of spadin or mixtures thereof of said at least one analog is selected from the group of: Ac-APLPRWSGPIGVSWGLR-NH$_2$ (SEQ ID NO:3), Ac-rlGwsvGipGswrplpa-NH$_2$ (SEQ ID NO:4), Ac-GVSWGLR-NH$_2$ (SEQ ID NO:5), Ac-IGVSWGLR-NH$_2$, (SEQ ID NO:6), Ac-rlGwsvGi-NH$_2$ (SEQ ID NO:7), Ac-QDRLAPPPPAAPLPRWSGPIGVSWGLR-NH$_2$ (SEQ ID NO:8), Ac-rlGwsvGipGswrplpaappppadlrdq-NH$_2$ (SEQ ID NO:9), Ac-APPPPAAPLPRWSGPIGVSWGLR-NH$_2$ (SEQ ID NO:10), Ac-rlGwsvGipGswrplpaappppa-NH$_2$ (SEQ ID NO:11), Ac-QDRLAPPPPAAPLPRWS-GPIGVSWGLRAAAAGGAFPRGGRWRR-NH$_2$ (SEQ ID NO:12), Ac-rrwrGGrpfaGGaaaarlGwsvGipGswrplpaapppp-padlrdq-NH$_2$ (SEQ ID NO:13), Ac-APLPRWSAPIA-VSWALR-NH$_2$ (SEQ ID NO:14), Ac-rlawsvaipaswrplpa-NH$_2$ (SEQ ID NO:15), c(rlGwsvGipGswrplpa) (SEQ ID NO:20), c(rlGwsvGipGswrplparlGwsvGipGswrplpa) (SEQ ID NO:21) and mixtures thereof.

A pharmaceutical composition is provided wherein the at least one analog of spadin or the at least one analog of a propeptide of spadin or mixtures thereof of said at least one analog is Ac-rlGwsvGipGswrplpa-NH$_2$ (SEQ ID NO:4) or Ac-rlGwsvGipGswrplpaappppadlrdq-NH$_2$ (SEQ ID NO:9) or Ac-rlGwsvGipGswrplpa-NH$_2$ (SEQ ID NO:4) and Ac-rlGwsvGipGswrplpaappppadlrdq-NH$_2$ (SEQ ID NO:9) is yet another aspect of the invention.

The pharmaceutical compositions, as described herein, contain acceptable vehicles such as distilled water, buffers, glycerol, polypropylene glycol, saline, phosphate buffered saline dextrose, ethanol and mixtures thereof.

In yet another aspect biodegradable pharmaceutical compositions are provided comprising at least one analog of spadin or at least one analog of a propeptide of spadin or mixtures thereof of said at least one analog in a biodegradable slow release vehicle comprising:

(a) a biodegradable triblock copolymer having the formula:

$$PLA_v\text{-}PEG_w\text{-}PLA_x$$

wherein v, w and x are the number of repeat units ranging from 4 to 1090 or 6 to 1090 and v=x or v≠x;

(b) a biodegradable diblock copolymer having the formula:

$$mPEG_y\text{-}PLA_z$$

wherein y and z are the number of repeat units ranging from 3 to 237 or 7 to 371, wherein the ratio of the biodegradable triblock copolymer of (a) and the biodegradable diblock copolymer of (b) is 1:3 to 1:8 or 1:1 to 1:19 or 3:2 to 1:19 in said biodegradable pharmaceutical composition.

The at least one analog of spadin or the at least one analogs of a propeptide of spadin or mixtures thereof of said at least one analog can be a retro-inverso peptide or an end-capped peptide in the biodegradable pharmaceutical compositions. When the at least one analog of spadin or the at least one analog of a propeptide of spadin or mixtures thereof of said at least one analog are end-capped, they are end-capped with an acetylated N-terminus or an amidated C-terminus or an acetylated N-terminus and an amidated C-terminus.

In another aspect biodegradable pharmaceutical compositions are provided wherein the at least one analog of spadin or the at least one analog of a propeptide of spadin or mixtures thereof of said at least one analog is selected from the group of: Ac-APLPRWSGPIGVSWGLR-NH$_2$ (SEQ ID NO:3), Ac-rlGwsvGipGswrplpa-NH$_2$ (SEQ ID NO:4), Ac-GVSWGLR-NH$_2$ (SEQ ID NO:5), Ac-IGVSWGLR-NH$_2$, (SEQ ID NO:6), Ac-rlGwsvGi-NH$_2$ (SEQ ID NO:7), Ac-QDRLAPPPPAAPLPRWSGPIGVSWGLR-NH$_2$ (SEQ ID NO:8), Ac-rlGwsvGipGswrplpaappppadlrdq-NH$_2$ (SEQ ID NO:9), Ac-APPPPAAPLPRWSGPIGVSWGLR-NH2 (SEQ ID NO:10), Ac-rlGwsvGipGswrplpaappppa-NH$_2$ (SEQ ID NO:11), Ac-QDRLAPPPPAAPLPRWSGPIGVSWGL-RAAAAGGAFPRGGRWRR-NH$_2$ (SEQ ID NO:12), Ac-rrwrGGrpfaGGaaaarlGwsvGipGswrplpaappppadlrdq-NH$_2$ (SEQ ID NO:13), Ac-APLPRWSAPIAVSWALR-NH$_2$ (SEQ ID NO:14), Ac-rlawsvaipaswrplpa-NH$_2$ (SEQ ID NO: 15), c(rlGwsvGipGswrplpa) (SEQ ID NO:20), c(rlGwsvGipGswrplparlGwsvGipGswrplpa) (SEQ ID NO:21) and mixtures thereof.

In yet another aspect a biodegradable pharmaceutical composition wherein the at least one analog of spadin or the at least one analog of a propeptide of spadin or mixtures thereof of said at least one analog is Ac-rlGwsvGipGswrplpa-NH$_2$ (SEQ ID NO:4) or Ac-rlGwsvGipGswrplpaappppadlrdq-NH$_2$ (SEQ ID NO:9) or Ac-rlGwsvGipGswrplpa-NH$_2$ (SEQ ID NO:4) and Ac-rlGwsvGipGswrplpaappppadlrdq-NH$_2$ (SEQ ID NO:9).

The biodegradable pharmaceutical compositions, as described herein, can be an injectable liquid at room temperature and forms an implant when injected into the body or are small solid particles or rod implants or spatial formulations.

The size of the polyethylene glycol chain ranges from 200 Da to 12 kDa or 194 Da to 12 kDa and the size of the end-capped polyethylene glycol chain ranges from 100 Da to 2 kDa or 164 to 2 kDA in the biodegradable pharmaceutical compositions, as described herein.

Furthermore, in the biodegradable pharmaceutical compositions, as described herein the analogs are present in an amount of 1% to 20% (w %/w %) of the total composition and the polymers are present in an amount of 20% to 50% (w %/w %) of the total composition, the triblock copolymer is present in an amount of 3.0% to 45% (w %/w %) of the total composition and the diblock copolymer is present in an amount of 8.0% to 50% (w %/w %) of the total composition.

In the biodegradable pharmaceutical compositions, as described herein, the polyester repeat unit to ethylene oxide molar ratio in the composition is between 0.5 to 3.5 or 0.5 to 22.3 in the triblock copolymer and 2 to 6 or 0.8 to 13 in the diblock copolymer.

A biodegradable pharmaceutical composition comprising Ac-rlGwsvGipGswrplpa-NH$_2$ (SEQ ID NO:4) or Ac-rlGwsvGipGswrplpaappppadlrdq-NH$_2$ (SEQ ID NO:9) or Ac-rlGwsvGipGswrplpa-NH$_2$ (SEQ ID NO:4) and Ac-rlGwsvGipGswrplpaappppadlrdq-NH$_2$ (SEQ ID NO:9) in a biodegradable slow release vehicle comprising (a) a biodegradable triblock copolymer having the formula:

$$PLA_v\text{-}PEG_w\text{-}PLA_x$$

wherein v, w and x are the number of repeat units ranging from 4 to 1090 or 6 to 1090 and v=x or v≠x;

(b) a biodegradable diblock copolymer having the formula:

$$mPEG_y\text{-}PLA_z$$

wherein y and z are the number of repeat units ranging from 3 to 237 or 7 to 371, wherein the ratio of the biodegradable triblock copolymer of (a) and the biodegradable diblock copolymer of (b) is 1:3 to 1:8 or 1:1 to 1:19 or 3:2 to 1:19 in said biodegradable pharmaceutical composition is yet another aspect of the present invention.

The biodegradable pharmaceutical compositions, as described herein, can be an injectable liquid at room temperature and forms an implant when injected into the body or are small solid particles or rod implants or spatial formulations.

The size of the polyethylene glycol chain ranges from 200 Da to 12 kDa or 194 Da to 12 kDa and the size of the end-capped polyethylene glycol chain ranges from 100 Da to 2 kDa or 164 to 2 kDA in the biodegradable pharmaceutical compositions, as described herein.

Furthermore, in the biodegradable pharmaceutical compositions, as described herein the analogs are present in an amount of 1% to 20% (w %/w %) of the total composition and the polymers are present in an amount of 20% to 50% (w %/w %) of the total composition, the triblock copolymer is present in an amount of 3.0% to 45% (w %/w %) of the total composition and the diblock copolymer is present in an amount of 8.0% to 50% (w %/w %) of the total composition.

In the biodegradable pharmaceutical compositions, as described herein, the polyester repeat unit to ethylene oxide molar ratio in the composition is between 0.5 to 3.5 or 0.5 to 22.3 in the triblock copolymer and 2 to 6 or 0.8 to 13 in the diblock copolymer.

A method for treating depression in an animal is another aspect of the present invention said method comprising administering to an animal in need of such treatment a pharmaceutically acceptable amount of at least one analog of spadin or at least one analog of a propeptide of spadin or mixtures thereof of said at least one analog and a pharmaceutically acceptable vehicle.

The at least one analog of spadin or the at least one analogs of a propeptide of spadin or mixtures thereof of said at least one analog can be a retro-inverso peptide or an end-capped peptide in the biodegradable pharmaceutical compositions. When the at least one analog of spadin or the at least one analog of a propeptide of spadin are end-capped, they are end-capped with an acetylated N-terminus or an amidated C-terminus or an acetylated N-terminus and an amidated C-terminus.

In another aspect in the method for treating depression in an animal the at least one analog of spadin or the at least one analog of a propeptide of spadin or mixtures thereof of said at least one analog is selected from the group of: Ac-APLPRWSGPIGVSWGLR-NH$_2$ (SEQ ID NO:3), Ac-rlGwsvGipGswrplpa-NH$_2$ (SEQ ID NO:4), Ac-GVSWGLR-NH$_2$ (SEQ ID NO:5), Ac-IGVSWGLR-NH$_2$ (SEQ ID NO:6), Ac-rlGwsvGi-NH$_2$ (SEQ ID NO:7), Ac-QDRLAP- PPPAAPLPRWSGPIGVSWGLR-NH$_2$ (SEQ ID NO:8), Ac-rlGwsvGipGswrplpaappppadlrdq-NH$_2$ (SEQ ID NO:9), Ac-APPPPAAPLPRWSGPIGVSWGLR-NH$_2$ (SEQ ID NO:10), Ac-rlGwsvGipGswrplpaapppa-NH$_2$ (SEQ ID NO:11), Ac-QDRLAPPPPAAPLPRWSGPIGVSWGLRAAAAGGAF-PRGGRWRR-NH$_2$ (SEQ ID NO:12), Ac-rrwrGGrpfaG-GaaaarlGwsvGipGswrplpaappppadlrdq-NH$_2$ (SEQ ID NO:13), Ac-APLPRWSAPIAVSWALR-NH$_2$ (SEQ ID NO:14), Ac-rlawsvaipaswrplpa-NH$_2$ (SEQ ID NO: 15), c(rl-GwsvGipGswrplpa) (SEQ ID NO:20), c(rlGwsvGipGswrplparlGwsvGipGswrplpa) (SEQ ID NO:21) and mixtures thereof.

In the method for treating depression in an animal, as described herein, the at least one analog of spadin or the at least one analog of a propeptide of spadin can be Ac-rlGwsvGipGswrplpa-NH$_2$ (SEQ ID NO:4) or Ac-rlGwsvGipGswrplpaappppadlrdq-NH$_2$ (SEQ ID NO:9) or Ac-rlGwsvGipGswrplpa-NH$_2$ (SEQ ID NO:4) and Ac-rlGwsvGipGswrplpaappppadlrdq-NH$_2$ (SEQ ID NO:9).

In the method for treating depression in an animal the pharmaceutically acceptable vehicle can be selected from the group of distilled water, buffers, glycerol, polypropylene glycol, saline, phosphate buffered saline dextrose, ethanol, organic solvents, as described herein and mixtures thereof.

A method for treating depression in a mammal, said method comprising administering to said animal in need of said treatment a pharmaceutically effective amount of a biodegradable pharmaceutical composition, as described herein, is also provided.

In yet another aspect, pharmaceutical compositions or biodegradable pharmaceutical compositions, as described herein, for the manufacture of a medicament to treat depression is provided.

A method for blocking TREK-1 channel activity is provided, in which the method comprising administering to an animal an effective amount of the compositions, pharmaceutical compositions and/or biodegradable compositions as described herein.

BRIEF DESCRIPTION OF THE DRAWINGS

FIG. 1 is a table showing the sequences of spadin analogs. Amino acids are presented in the one letter symbols. Peptide sequences are presented using the one-letter nomenclature. Amino acids in L-configuration are shown in capital letters while amino acids in D-configuration are shown as lowercase. Ac- corresponds to acetyl group, —NH2 to an amide group. SEQ ID Nos. 1 to 15 are derived from human sequences. In SEQ ID Nos. 14 and 15 the Glycine (G) in these sequences has been substituted to Alanine (A). SEQ ID NOs. 16 and 17 are derived from rodents, while SEQ ID NOs. 18 and 19 are derived from dogs. SEQ ID NOs 20 is a head to tail cyclized version of SEQ ID No 4, SEQ ID NOs 21 is a head to tail cyclized version of a dimer of SEQ ID No 4. SEQ ID NOs 22 is a head to tail cyclized version of SEQ ID No 15, SEQ ID NOs 23 is a head to tail cyclized version of a dimer of SEQ ID No 15.

FIG. 2A are various I=f(V) in which all currents were measured in the presence of a mixture of K+ channel blockers. Control currents (K+ channel blockers alone) are black filled circles, and 10 μm arachidonic acid amplified currents (K+ channel blocker+AA), are represented by white filled circles, 10 μm arachidonic acid amplified currents in the presence of 100 nM spadine or its analogs (K+ blockers+AA+analog) are represented by the black filled triangles. FIG. 2B is a graph showing the percentage of inhibition of the TREK-1 current measured at 0 mV obtained by application of 100 nM of spadin and its analogs. FIG. 2C are dose-response curves obtained by measuring the % of TREK-1 current inhibition at 0 mV with Analog2 (SEQ ID:3, white filled circles), Analog 3 (SEQ ID NO:4, black filled circles), Analog 7 (SEQ ID NO:8, white filled squares) and Analog 8 (SEQ ID NO:9, black filled squares). The analogs in this figure correspond to the following SEQ ID Nos: analog 2 (SEQ ID NO:3), analog 3 (SEQ ID NO:4), analog 4 (SEQ ID NO:5), analog 5 (SEQ ID NO:6), analog 6 (SEQ ID NO:7), analog 7 (SEQ ID NO:8), analog 8 (SEQ ID NO:9), analog 9 (SEQ ID NO:10), analog 10 (SEQ ID NO:11), analog 11 (SEQ ID NO:12) and analog 12 (SEQ ID NO:13).

FIG. 3A is a graph showing the results of a Forced Swimming Test (FST) performed after an acute treatment. Immobility times were measured 30 minutes after the i.v. injection of the drugs at a dose of 10 μg/kg in a single bolus of 100 μL of NaCl 0.9%. FIG. 3B is a graph showing the results of a Forced Swimming Test (FST) performed after a sub-chronic treatment (4 days, 4 d). Immobility times were measured on the $5^{th}$ day after a daily i.v. injection of drugs at a dose of 10 μg/kg in a single bolus of 100 μL of NaCl 0.9% for 4 days. FIG. 3C is a graph showing the results of a Novelty Suppressed Feeding test (NSF) performed after a sub-chronic treatment (4 days, 4 d). Latencies to feed were measured on the $5^{th}$ day after a daily i.v. injection of drug at a dose of 10 μg/kg in a single bolus of 100 μL of NaCl 0.9% for 4 days. FIG. 3D and FIG. 3E are Learned Helplessness Tests (LHT) performed after a sub-chronic treatment (4 days, 4 d). Latencies to feed were measured on the $5^{th}$ day after a daily i.v. injection of drugs at a dose of 10 μg/kg in a single bolus of 100 μL of NaCL 0.9% for 4 days. FIG. 3D is a graph showing mean escape latencies for the entire experiment. FIG. 3E is a curve showing the mean escape latencies by blocks of 5 trials.*, p<0.05, , p<0.01, *, p<0.001.

FIG. 4A shows in vivo duration of action of spadin (A). FIG. 4B shows the in vivo duration of action of Analog 3 (SEQ ID:4) and Analog 8 (SEQ ID:9). For each drug at each times, animals were naïve.*, p<0.05, , p<0.01, *, p<0.001, ns means non specific.

FIG. 5A is a graph showing the quantitation of 5-bromo-2-deoxyuridine (BrdU) positive cells of hippocampus treated with saline, spadin or Analog 3 (SEQ ID NO:4) or analog 8 (SEQ ID NO:9) for 4 consecutive days by an i.v. injection of drugs at a dose of 10 μg/kg in a single bolus of 100 μL of NaCl 0.9%. FIG. 5B are photomicrographs of BrdU-labeled neurons in the dentate gyrus of the mouse hippocampus treated for 4 days either with saline or spadin or Analog 3 (SEQ ID NO:4) or Analog 8 (SEQ ID NO:9) by an i.v. injection at a dose of 10 μg/kg for all drugs. Arrows showed examples of positive cells. *, p<0.05, , p<0.01*.

FIG. 6A is a graph showing the results of a Tail flick test (n=10 per group). For each mouse the time to withdraw its tail immersed in a water bath at 50° C. was measured twice and averaged. There was no significant difference between saline and spadin or both Analog 3 (SEQ ID NO:4) and Analog 8 (SEQ ID NO:9) treated mice. FIG. 6B is a graph showing the results of an epilepsy test. Seizures were triggered by an i.p. injection of kainate (25 mg/kg) that immediately followed an i.v. injection of saline solution or Analog 3 (SEQ ID NO:4) at a dose of 1 or 10 μg/kg in 100 μl bolus (n=10 per group). The number of animals reaching the different levels of severity was counted. FIG. 6C is a graph showing the Analog 3 (SEQ ID NO:4) effects on the cardiac delayed $K^+$ rectifier current $I_{kr}$. Typical traces of human whole cell hERG (human Ether a go-go Related Gene) current recordings in the absence (control)(a) or in the presence of 10 μM of Analog 3 (SEQ ID NO:4) (b). (c) and (d) are IN curves obtained with the first pulse (c, end of pulse) and the second pulse (d, tail current) of hERG current (n=5). FIG. 6D is a graph showing the Analog 3 (SEQ ID NO:4) effects on the cardiac delayed $K^+$ rectifier current $I_{ks}$. Typical traces of human whole cell human-IKS current recordings in the absence (control)(a) or in the presence of 10 μM of Analog 3 (SEQ ID NO:4) (b). (c) and (d) are IN curves obtained with the first pulse (c, end of pulse) and the second pulse (d, tail current) of human-IKS current (n=5).

FIG. 8A corresponds to analog 13 (SEQ ID NO:14), FIG. 8B to analog 14 (SEQ ID NO:15), FIG. 8C to analog 15 (SEQ ID NO:16), FIG. 8D to analog 16 (SEQ ID NO:17). FIG. 8E is a graph showing the percentage of inhibition of the TREK-1 current measured at 0 mV obtained by application of 100 nM of analogs 13 to 16. FIG. 8F are dose-response curves obtained by measuring the % of TREK-1 current inhibition at 0 mV with analog 13 (white filled circles), analog 14 (black filled circles), analog 15 (black filled squares) and analog 16 (white filled squares).

DESCRIPTION OF THE PREFERRED EMBODIMENTS

Figure 2:
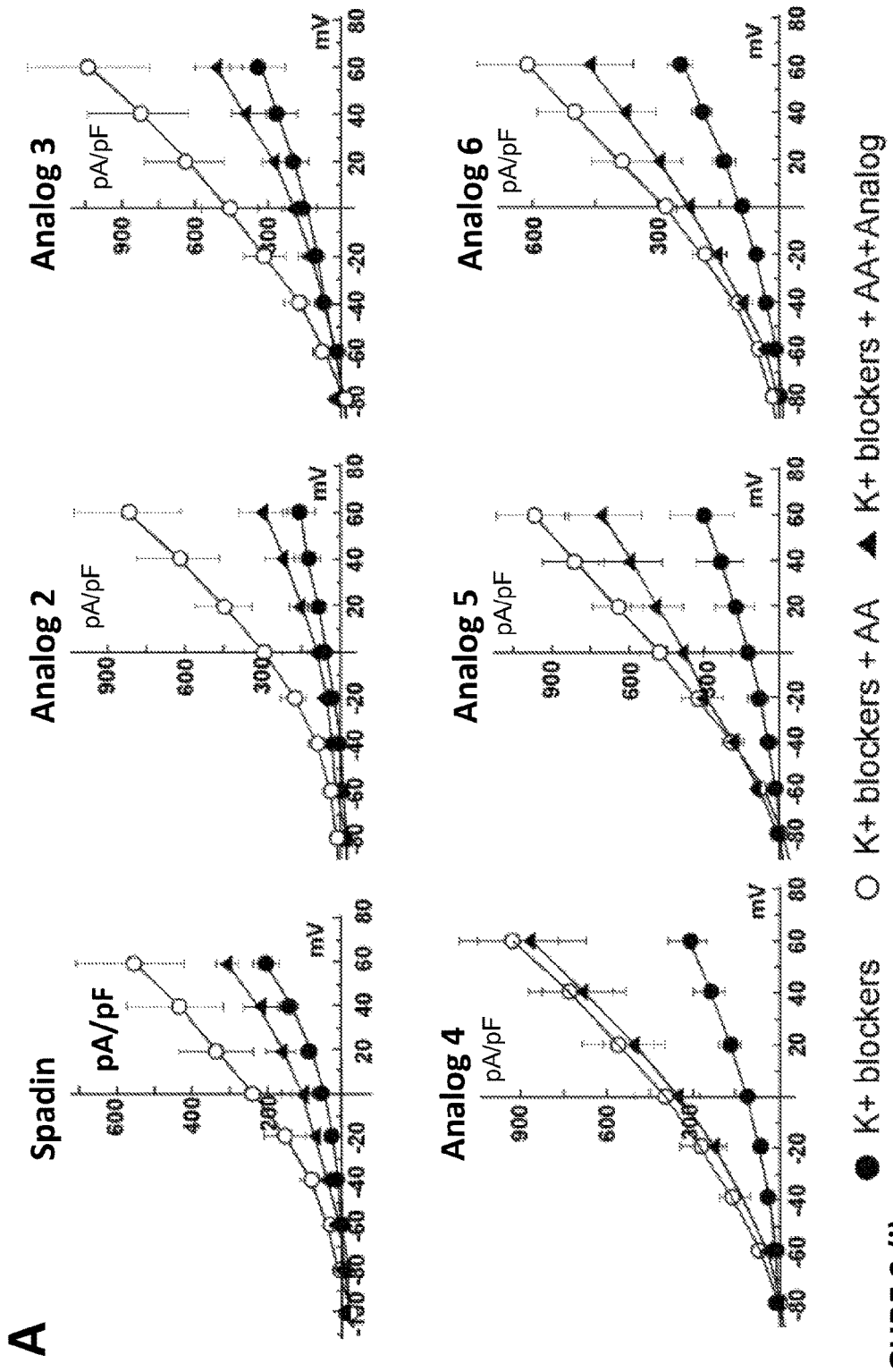
FIG. 2 shows I=f(V) curves of spadin and its analogs. All experiments were performed on h-TREK-1/HEK cell line in the presence of a mixture of K+ channels blockers and by using the whole cell configuration of the patch-clamp technique.

As used herein, the term "analog" or "peptide analog" means a compound that is similar to but not identical with another compound. In this regard a "peptide analog" as described herein means a peptide that has been modified from spadin which has the sequence APLPRWS-GPIGVSWGLR (SEQ ID NO:1) or the full spadin propeptide having the sequence QDRLDAPPPPAAPLPRWS-GPIGVSWGLRAAAAGGAFPRGGRWRR (SEQ ID NO:2).

The preferred method for manufacturing the analogs of the present invention is via chemical synthesis in preferable solid phase. Any synthesis technique can be used and these techniques are known by persons skilled in the art. By way of example, the peptides can be sequenced using the procedure described in Krieger et al, "Affinity purification of synthetic peptides." PNAS 73:3160-3164 (1976).

By "modified" is meant to change in form or character generally by peptidomimetic chemistries such as the use of D-amino acids, unnatural amino acids, peptide backbone modifications, cyclizations, secondary structure-inducing templates and end-capped peptides. The term "modified" includes peptide retro-inverso isomerization.

A "retro-inverso peptide", as used herein means a peptide that is made up of D-amino acids in a reversed sequence and, when extended assumes a side chain topology similar to that of the parent peptide but with inverted amide peptide bonds. In this regard, the L-amino acids, as described herein, are in uppercase, while the D-amino acids, as described herein, are in lower case.

Processes to make retro-inverso spadin analogs, for example is via the procedure of Bonelli et al, "Solid Phase synthesis of retro-inverso peptide analogs," Int. J. Peptide-Protein Res. 24, 553-556 (1984); Verdini and Visomi, "Synthesis, resolution and assignment of configuration of potent hypotensive retro-inverso bradykinin potentiating peptide 5a (BPP5a) analogs," J. Chem. Soc. Perkin Trans I 607-701 (1985).

The fraction of an administered dose of unchanged drug that reaches the systemic circulation and is one of the principle pharmacokinetic properties of drugs is the definition for "bioavailability" as used herein.

The phrase "end-capped", as used herein, refers to a peptide which has been modified at the N-terminus and/or the C-terminus. End-capped refers to the attachment of a chemical moiety to the terminus, so as to form a cap. The end-capped modification typically results in masking the charge of the peptide terminus, and/or altering chemical features thereof, such as, hydrophobicity, hydrophilcity, reactivity, solubility and the like. End-capping also limits the exopeptidase activity. Examples of moieties suitable for peptide end-capping modification can be found, for example, in Green et al., "Protective Groups in Organic Chemistry", (Wiley, 2.sup.nd ed. 1991) and Harrison et al., "Compendium of Synthetic Organic Methods", Vols. 1-8

(John Wiley and Sons, 1971-1996). In one aspect, the peptide can be end-capped by acetylation at the N-terminus or amidated at the C-terminus or both acetylated at the N-terminus and amidated at the C-terminus.

By "spadin analog activity" refers to both spadin analogs and spadin propeptide analogs or mixtures thereof which show increased affinity for TREK-1 channels and an increased bioavailability compared to their spadin or spadin propeptide counterparts.

The term "animals" encompasses all members of the Kingdom Animalia.

As described herein, "depression" means an illness that involves the body, mood and thoughts of an animal and affects the way the animal eats, sleeps, feels and thinks about things. For example in humans signs of depression include loss of interest in activities that were once interesting or enjoyable, loss of appetite, weight loss or overeating causing weight gain, loss of emotional expression, persistently sad, anxious or moody, feelings of hopelessness, pessimism, guilt, worthlessness or helplessness, social withdrawal, unusual fatigue, low energy levels, a feeling of being slowed down, sleep disturbance and insomnia, trouble concentrating, remembering or making decisions; unusual restlessness or irritability, persistent physical problems such as headaches, digestive disorders or chronic pain.

Depression is not limited to humans but can also be present in other animals such as dogs, cats, horses, monkeys, rats, birds and the like. The common signs of depression in dogs, for example, include becoming withdrawn, becoming inactive, changes in appetite, and changes in sleep habits.

The term "depression" encompasses all different types of depression including Hypomania, Cyclothymia, Major Depression, Unipolar Disorder, Dysthymic Disorder, Neurasthenia, Bipolar Disorder, Rapid Cycling Bipolar Disorder, Bipolar II Disorder, Adolescent bipolar disorder, Bipolar affective disorder, Children Bipolar Disorder, Manic Depressive Disorder, Postpartum Depression, Melancholia, Agitated Depression, Manic Depressive Psychosis, Depressive Disorder NOS, Dysphoric Mania, Neurotic depression, Masked depression, Endogenous depression, Puerperal psychosis, Postpartum psychosis, Winter depression—Seasonal Affective Disorder (SAD), Post Traumatic Stress Disorder, Premenstrual Dysphoric Disorder (PMDD), Atypical depression and Alcohol Depression.

By "pharmaceutically acceptable amount" means an amount that is administered to an animal that is sufficient to in fulfill its pharmaceutical purpose; i.e., to treat depression. This amount may differ according to the size and weight of the animal.

The term "treat" as used herein encompasses (1) delaying or preventing the onset of depression or (2) slowing or stopping the progression, aggravation or deterioration of depression or (3) bringing about or ameliorating the symptoms of depression.

By "effective amount" means any amount of analogs spadin or analogs of a propeptide of spadin or mixtures thereof that is sufficient to fulfill its intended purpose; i.e., to block TREK-1 channel activity.

By "at least one" when referring to the analogs of spadin or analogs of a propeptide of spadin or mixtures thereof means that one analog of spadin and up to 16 analogs of spadin can be used in the formulation. The same applies to analogs of a propeptide of spadin and mixtures of spadin analogs and propeptide of spadin analogs. Thus, 1, 2, 3, 4, 5, 6, 7, 8, 9, 10, 11, 12, 13, 14, 15 and 16 analogs of spadin or analogs of a propeptide of spadin or mixtures thereof can be formulated in the compositions, as described herein, the pharmaceutical compositions, as described herein, and the biodegradable pharmaceutical compositions, as described herein, as well as being used in the methods as described herein.

By "consisting essentially of" as used herein means that additional amino acids can be added or deleted or modified to another amino acid from the spadin analogs or spadin propeptide analogs or mixtures thereof, but does not change the analogs activity. For example, conservative amino acid modifications may be made, which although they alter the primary sequence of the peptide, do not normally alter its function. Conservative amino acid substitutions typically include substitutions within the following groups: glycine, alanine; valine, isoleucine, leucine; aspartic acid, glutamic acid; asparagine, glutamine, serine, threonine, lysine, arginine; phenylalanine and tyrosine.

A composition comprising at least one analog of spadin or at least one analog of a propeptide of spadin or mixtures thereof of said at least one analog and an acceptable vehicle is one aspect of the present invention. In this aspect, the at least one analog of spadin or the at least one analog of a propeptide of spadin or mixtures thereof of said at least one analog is a retro-inverso peptide or the at least one analog of spadin or the at least one analog of a propeptide of spadin or mixtures thereof of said at least one analog is end-capped. When the at least one analog of spadin or the at least one analog of a propeptide of spadin or mixtures thereof of said at least one analog is end-capped, it can be end-capped with an acetylated N-terminus or an amidated C-terminus or an acetylated N-terminus and an amidated C-terminus.

In one aspect the at least one analog of spadin or the at least one analog of a propeptide of spadin or mixtures thereof of said at least one analog is selected from the group of: Ac-APLPRWSGPIGVSWGLR-NH$_2$ (SEQ ID NO:3), Ac-rlGwsvGipGswrplpa-NH$_2$ (SEQ ID NO:4), Ac-GVSWGLR-NH$_2$ (SEQ ID NO:5), Ac-IGVSWGLR-NH$_2$, (SEQ ID NO:6), Ac-rlGwsvGi-NH$_2$ (SEQ ID NO:7), Ac-QDRLAPPPPAAPLPRWSGPIGVSWGLR-NH$_2$ (SEQ ID NO:8), Ac-rlGwsvGipGswrplpaappppadlrdq-NH$_2$ (SEQ ID NO:9), Ac-APPPPAAPLPRWSGPIGVSWGLR-NH2 (SEQ ID NO:10), Ac-rlGwsvGipGswrplpaapppppa-NH$_2$ (SEQ ID NO:11), Ac-QDRLAPPPPAAPLPRWS-GPIGVSWGLRAAAAGGAFPRGGRWRR-NH2 (SEQ ID NO:12), Ac-rrwrGGrpfaGGaaaarlGwsvGipGswrplpaappp-padlrdq-NH$_2$ (SEQ ID NO:13), Ac-APLPRWSAPIA-VSWALR-NH$_2$ (SEQ ID NO:14), Ac-rlawsvaipaswrplpa-NH$_2$ (SEQ ID NO: 15), c(rlGwsvGipGswrplpa) (SEQ ID NO:20), c(rlGwsvGipGswrplparlGwsvGipGswrplpa) (SEQ ID NO:21) and mixtures thereof.

In yet another aspect the at least one analog of spadin or the at least one analog of a propeptide of spadin is Ac-rlGwsvGipGswrplpa-NH$_2$ (SEQ ID NO:4) or Ac-rlGwsv-GipGswrplpaappppadlrdq-NH$_2$ (SEQ ID NO:9) or Ac-rlG-wsvGipGswrplpa-NH$_2$ (SEQ ID NO:4) and Ac-rlGwsvGipGswrplpaappppadlrdq-NH$_2$ (SEQ ID NO:9).

The compositions, as described herein, are in an acceptable vehicle. Any acceptable vehicle that does not destroy the physiological characteristics of spadin analogs or analogs of preprospadin or mixtures thereof can be used. Examples include distilled water, buffers, glycerol, polypropylene glycol, saline, phosphate buffered saline dextrose, ethanol, adjuvants, organic solvents such as benzyl alcohol, benzyl benzoate, diethylene glycol dimethyl ether (Diglyme), diethylene glycol monoethyl ether (DEGMEE), dimethyl isosorbide (DMI), dimethyl sulfoxide (DMSO), ethyl acetate, ethyl benzoate, ethyl lactate, ethylene glycol monoethyl ether acetate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin (tripro), or triethylene glycol dimethyl ether (triglyme) and mixtures thereof and mixtures of the acceptable vehicle.

The acceptable vehicle is present in an amount of 0.5 ml to 3 ml. In another aspect the acceptable vehicle is present in an amount of 0.01 ml to 2 ml. In yet another aspect, the acceptable vehicle is present in an amount of 0.005 ml to 2.5 ml.

The compositions of the present invention can be used for a variety of purposes such as to make polyclonal and monoclonal antibodies against the analogs of spadin, as described herein or analogs of a propeptide of spadin, as described herein, or mixtures thereof of said analogs of spadin and propeptide of spadin, as described herein. The polyclonal or monoclonal antibodies can be used in research to identify or quantify the spadin analogs, as described herein, or propeptide analogs of spadin, as described herein, or mixtures thereof of said at least one analog. They can also be used in diagnostics to test the presence and levels of the analogs of spadin, as described herein, or analogs of propeptide spadin, as described herein, or mixtures of the analogs, as described herein, in a biological sample from an animal.

The compositions, described herein, can be labeled and used as a probe to test for the quantity of the analogs of spadin, as described herein or analogs of a propeptide of spadin, as described herein, or mixtures thereof of the analogs, as described herein, for use in research or in diagnostics. The compositions, as described herein can be labeled with a fluorescent label, chemiluminescent agents, ligands, radionuclides, a phosphorescent groups, dyes, radioactivity such as $^{32}P$, $^{3}H$, $^{18}F$, $^{35}S$, $^{135}I$, $^{125}I$, $^{123}I$, $^{64}Cu$, $^{187}Re$, $^{111}IN$, $^{90}Y$, $^{99m}Tc$, $^{177}Lu$ and $^{14}C$, biotin/streptavidin, enzymes and the like. The probes can be used in immunoassay such as RIA, ELISA, EIA and the like. They are used to test a biological sample in an animal or for research purposes.

In the diagnostic aspect of the invention, as described herein, the biological sample is any biological sample that comes from an animal. These biological samples include blood, plasma, tissue, urine cerebral spinal fluid, hair, nails and the like.

The invention also includes kits. The kits can contain the compositions of the present invention and an acceptable vehicle. The kits, may, for example contain a sole vial with the combined composition and acceptable vehicle. Alternatively, there may be two separate vials containing the compositions in one vial and the acceptable vehicle in another.

Besides the compositions, the monoclonal and/or polyclonal antibodies can be present in a kit with the reagents necessary for carrying out the immune reaction or the probes can also be present in kits with the necessary reagents.

A pharmaceutical composition comprising at least one analog of spadin or at least one analog of a propeptide of spadin or mixtures thereof of said at least one analog and a pharmaceutically acceptable vehicle is yet another aspect of the present invention. In this aspect, the at least one analog of spadin or the at least one analog of a propeptide or spadin or mixtures thereof of said at least one analog is a retro-inverso peptide or it can be end-capped.

The pharmaceutical composition is end-capped with an acetylated N-terminus or an amidated C-terminus or an acetylated N-terminus and an amidated C-terminus.

The pharmaceutical composition comprises the at least one analog of spadin or the at least one analog of a propeptide of spadin or mixtures thereof of said at least one analog, which is selected from the group of: Ac-APLPRWS-GPIGVSWGLR-NH$_2$ (SEQ ID NO:3), Ac-rlGwsvGipGswrplpa-NH$_2$ (SEQ ID NO:4), Ac-GVSWGLR-NH$_2$ (SEQ ID NO:5), Ac-IGVSWGLR-NH$_2$, (SEQ ID NO:6), Ac-rlGwsvGi-NH$_2$ (SEQ ID NO:7), Ac-QDRLAPPPPAAPLPRWS-GPIGVSWGLR-NH$_2$ (SEQ ID NO:8), Ac-rlGwsvGipGswrplpaappppadlrdq-NH$_2$ (SEQ ID NO:9), Ac-APPPPAAPLPRWSGPIGVSWGLR-NH$_2$ (SEQ ID NO:10), Ac-rlGwsvGipGswrplpaappppa-NH$_2$ (SEQ ID NO:11), Ac-QDRLAPPPPAAPLPRWSGPIGVSWGL-RAAAAGGAFPRGGRWRR-NH$_2$ (SEQ ID NO:12), Ac-rrwrGGrpfaGGaaaarlGwsvGipGswrplpaappppadlrdq-NH2 (SEQ ID NO:13), Ac-APLPRWSAPIAVSWALR-NH$_2$ (SEQ ID NO:14), Ac-rlawsvaipaswrplpa-NH$_2$ (SEQ ID NO: 15), c(rlGwsvGipGswrplpa) (SEQ ID NO:20), c(rlGwsvGipGswrplparlGwsvGipGswrplpa) (SEQ ID NO:21) and mixtures thereof.

In another aspect the pharmaceutical composition comprises the at least one analog of spadin or the at least one analog of a propeptide of spadin is Ac-rlGwsvGipGswrplpa-NH$_2$ (SEQ ID NO:4) or Ac-rlGwsvGipGswrplpaappppadl-rdq-NH$_2$ (SEQ ID NO:9) or Ac-rlGwsvGipGswrplpa-NH$_2$ (SEQ ID NO:4) and Ac-rlGwsvGipGswrplpaappppadlrdq-NH$_2$ (SEQ ID NO:9).

The pharmaceutically acceptable vehicle in the pharmaceutical composition is selected from the group of distilled water, buffers, glycerol, polypropylene glycol, saline, phosphate buffered saline dextrose, ethanol, adjuvants organic solvents such as benzyl alcohol, benzyl benzoate, diethylene glycol dimethyl ether (Diglyme), diethylene glycol monoethyl ether (DEGMEE), dimethyl isosorbide (DMI), dimethyl sulfoxide (DMSO), ethyl acetate, ethyl benzoate, ethyl lactate, ethylene glycol monoethyl ether acetate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin (tripro), or triethylene glycol dimethyl ether (triglyme) and mixtures thereof and mixtures of the pharmaceutically acceptable vehicles.

The pharmaceutical compositions according to the present invention comprise at least one analog of spadin or at least one analog of a prepeptide of spadin or mixtures thereof of said at least one analog according to the present invention in an amount effective to achieve desirable results and they may be administered as unit dosage forms (for example, in a solid, semi-solid or liquid forms). The at least one analog, as described herein, can be in a mixture with a carrier or excipient suitable for intramuscular, intravenous, oral, sublingual, inhalation and intrarectal administration. The at least one analog of spadin or at least one analog of a propeptide of spadin or mixtures thereof of said at least one analog can be combined with usually used non-toxic pharmaceutically acceptable carriers suitable for preparing solutions, tablets, pellets, capsules, dragee, suppositories, emulsions, suspensions, ointments, gels and any other dosage forms.

As excipients different substances may be used such as saccharides, e.g., glucose, lactose or sucrose, mannitol or sorbitol, cellulose derivatives and/or calcium phosphates, e.g., tricalcium phosphate or acidic calcium phosphate; as a binder, may be used such substances as a starch paste, e.g., corn, wheat, rice, potato starch, gelatin, tragacant, methylcellulose, hydroxypropylmethylcellulose, sodium carboxymethylcellulose and/or polyvinylpyrrolidone. When necessary, disintegrants may be used such as the above mentioned starches and carboxymethylstarch, cross-linked polyvinylpyrrolidone, agar or alginic acid or a salt thereof such as sodium alginate.

Optional additives such as agents regulating fluidity and lubricants such as silica dioxide, talc, stearic acid and salts thereof such as magnesium stearate or calcium stearate and/or propyleneglycol may be used in the formulation.

A dragee core is usually coated by a layer, which is resistant to action of gastric juice. For this purpose, concentrated solutions of saccharides may be used which may optionally comprise gum Arabic, talc, polyvinylpyrrolidone, polyethyleneglycol and/or titanium dioxide and suitable organic solvents or mixtures thereof.

As additives, stabilizers, thickeners, dyes and flavors may be also used.

As an ointment base, carbohydrate ointment bases such as white and yellow Vaseline (Vaselinum album, Vaselinum flavum), Vaseline ointment (Oleum Vaselini), white and yellow ointment (Unguentum album, Unguentum flavum), and as additives for imparting a more compact consistence additives such as hard paraffin and wax may be used; absorptive ointment bases such as hydrophilic Vaseline (Vaselinum hydrophylicum), lanoline (Lanolinum), cold creme (Unguentum leniens) may be used; ointment bases washable by water such as hydrophilic ointment (Unguentum hydrophylicum) may be used; water-soluble ointment bases such as polyethyleneglycol ointment (Unguentum Glycolis Polyethyleni), bentonite bases and other may be used.

As a base for gels, methylcellulose, carboxymethylcellulose sodium salt, oxypropylcellulose, polyethyleneglycol or polyethylene oxide, carbopol may be used.

As a base for suppositories, bases insolvable in water such as cocoa butter; bases soluble in water or mixable with water such as gelatin-glycerol or polyethylene oxide; combine bases, e.g., saponaceous-glycerinic bases may be used.

In manufacturing a unit dosage form, the analogs and mixtures of analogs, as described herein, may be used in a combination with a carrier may vary depending on recipient being treated, a particular mode of administering a medicament.

Thus, for example, in using the analogs of the present invention in the form of solutions for injections, the content of the at least one analog of spadin or the at least one analog of a propeptide of spadin or mixtures thereof of said at least one analog is 0.005 to 20%. As dilutors, 0.9% sodium chloride solution, distilled water, novocaine solution for injections, Ringer solution, glucose solution, specific additives for dissolution may be used. In administering compounds of the present invention into the body in the form of tablets and suppositories, their amount is 5.0-500 mg per an unit dosage form.

Dosage forms of the present invention are manufactured according to standard techniques such as e.g., processes of mixing, granulation, formation of dragee, dissolution and freeze drying.

In yet another aspect of the invention a biodegradable pharmaceutical composition comprising at least one analog of spadin or at least one analog of a propeptide of spadin or mixtures thereof of said at least one analog in a biodegradable slow release vehicle comprising:

(b) a biodegradable triblock copolymer having the formula:

wherein v, w and x are the number of repeat units ranging from 4 to 1090 or 6 to 1090 and v=x or v≠x;

(b) a biodegradable diblock copolymer having the formula:

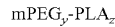

wherein y and z are the number of repeat units ranging from 3 to 237 or 7 to 371, wherein the ratio of the biodegradable triblock copolymer of (a) and the biodegradable diblock copolymer of (b) is 1:3 to 1:8 or 1:1 to 1:19 or 3:2 to 1:19 in said biodegradable pharmaceutical composition is provided.

These biodegradable pharmaceutical composition are described in WO20012/090070, which is incorporated herein by reference.

The biodegradable pharmaceutical composition comprises the at least one analog of spadin or at least one analog of a propeptide of spadin or mixtures thereof of said at least one analog, which is a retro-inverso peptide or these analogs can be end-capped peptides. The at least one analog of spadin or at least one analog of a propeptide of spadin or mixtures thereof of said at least one analog is end-capped with an acetylated N-terminus or an amidated C-terminus or an acetylated N-terminus and an amidated C-terminus.

The biodegradable pharmaceutical composition comprising the at least one analog of spadin or at least one analog of a propeptide of spadin or mixtures thereof of said at least one analog, is selected from the group of: Ac-APLPRWS-GPIGVSWGLR-$NH_2$ (SEQ ID NO:3), Ac-rlGwsvGipGswr-plpa-$NH_2$ (SEQ ID NO:4), Ac-GVSWGLR-$NH_2$ (SEQ ID NO:5), Ac-IGVSWGLR-$NH_2$, (SEQ ID NO:6), Ac-rlGwsvGi-$NH_2$ (SEQ ID NO:7), Ac-QDRLAPPPPAAPLPRWS-GPIGVSWGLR-$NH_2$ (SEQ ID NO:8), Ac-rlGwsvGipGswr-plpaappppadlrdq-$NH_2$ (SEQ ID NO:9), Ac-APPPPAAPLPRWSGPIGVSWGLR-$NH_2$ (SEQ ID NO:10), Ac-rlGwsvGipGswrplpaapppa-$NH_2$ (SEQ ID NO:11), Ac-QDRLAPPPPAAPLPRWSGPIGVSWGL-RAAAAGGAFPRGGRWRR-$NH_2$ (SEQ ID NO:12), Ac-rrwrGGrpfaGGaaaarlGwsvGipGswrplpaappppadlrdq-$NH_2$ (SEQ ID NO:13), Ac-APLPRWSAPIAVSWALR-$NH_2$ (SEQ ID NO:14), Ac-rlawsvaipaswrplpa-$NH_2$ (SEQ ID NO: 15), c(rlGwsvGipGswrplpa) (SEQ ID NO:20), c(rlGwsv-GipGswrplparlGwsvGipGswrplpa) (SEQ ID NO:21) and mixtures thereof.

In another embodiment the biodegradable pharmaceutical composition comprises Ac-rlGwsvGipGswrplpa-$NH_2$ (SEQ ID NO:4) or Ac-rlGwsvGipGswrplpaappppadlrdq-$NH_2$ (SEQ ID NO:9) or Ac-rlGwsvGipGswrplpa-$NH_2$ (SEQ ID NO:4) and Ac-rlGwsvGipGswrplpaappppadlrdq-$NH_2$ (SEQ ID NO:9).

The biodegradable pharmaceutical compositions, as described herein, can be an injectable liquid at room temperature and forms an implant when injected into the body or are small solid particles or rod implants or spatial formulations.

With respect to the biodegradable pharmaceutical compositions, as described herein, the size of the polyethylene glycol chain ranges from 200 Da to 12 kDa or 194 Da to 12 kDa and the size of the end-capped polyethylene glycol chain ranges from 100 Da to 2 kDa or 164 to 2 kDA and the polymers are present in an amount of 20% to 50% (w %/w %) of the total composition.

In the biodegradable pharmaceutical compositions the triblock copolymer is present in an amount of 3.0% to 45% (w %/w %) of the total composition and the diblock copolymer is present in an amount of 8.0% to 50% (w %/w %) of the total composition.

Furthermore, the polyester repeat unit to ethylene oxide molar ratio in the biodegradable pharmaceutical composition is between 0.5 to 3.5 or 0.5 to 22.3 in the triblock copolymer and 2 to 6 or 0.8 to 13 in the diblock copolymer in the biodegradable slow release vehicle as described herein.

The at least one analog of spadin or at least one analog of a propeptide of spadin or mixtures thereof of said at least one analog are present in an amount of 0.005 to 20% (w %/w %) of the total biodegradable pharmaceutical composition.

The at least one analog of spadin or at least one analog of a propeptide of spadin or mixtures thereof of said at least one analog a can be released for a duration of between 7 days to 1 year or longer depending upon the type of treatment needed and the biodegradable pharmaceutical composition used. In one aspect the biodegradable pharmaceutical composition can deliver the at least one analog of spadin or at least one analog of a propeptide of spadin or mixtures thereof of said at least one analog for at least 7 days. In another aspect the biodegradable pharmaceutical composition can deliver the at least one analog of spadin or at least one analog of a propeptide of spadin or mixtures thereof of said at least one analog for at least 30 days. In one aspect the biodegradable pharmaceutical composition can deliver the at least one analog of spadin or at least one analog of a propeptide of spadin or mixtures thereof of said at least one analog for at least 90 days. In yet another aspect the biodegradable pharmaceutical composition can deliver the at least one analog of spadin or at least one analog of a propeptide of spadin or mixtures thereof of said at least one analog for 3 to 6 months or longer.

In another aspect, a method for treating depression in an animal said method comprising administering to an animal in need of such treatment a pharmaceutically acceptable amount of at least one analog of spadin or at least one analog of a propeptide of spadin or mixtures thereof of said at least one analog and a pharmaceutically acceptable vehicle is provided. In this method the at least one analog of spadin or at least one analog of a propeptide of spadin or mixtures thereois a retro-inverso peptide or can be an end-capped peptide. When the analogs described herein are end-capped, they can be end-capped with an acetylated N-terminus or an amidated C-terminus or an acetylated N-terminus and an amidated C-terminus.

In this method for treating the at least one analog of spadin or at least one analog of a propeptide of spadin or mixtures thereof of said at least one analog is selected from the group of: Ac-APLPRWSGPIGVSWGLR-NH$_2$ (SEQ ID NO:3), Ac-rlGwsvGipGswrplpa-NH$_2$ (SEQ ID NO:4), Ac-GVSWGLR-NH$_2$ (SEQ ID NO:5), Ac-IGVSWGLR-NH$_2$, (SEQ ID NO:6), Ac-rlGwsvGi-NH$_2$ (SEQ ID NO:7), Ac-QDRLAPPPPAAPLPRWSGPIGVSWGLR-NH$_2$ (SEQ ID NO:8), Ac-rlGwsvGipGswrplpaappppadlrdq-NH$_2$ (SEQ ID NO:9), Ac-APPPPAAPLPRWSGPIGVSWGLR-NH$_2$ (SEQ ID NO:10), Ac-rlGwsvGipGswrplpaapppa-NH$_2$ (SEQ ID NO:11), Ac-QDRLAPPPPAAPLPRWSGPIGVSWGL-RAAAAGGAFPRGGRWRR-NH$_2$ (SEQ ID NO:12), Ac-rrwrGGrpfaGGaaaarlGwsvGipGswrplpaappppadlrdq-NH2 (SEQ ID NO:13), Ac-APLPRWSAPIAVSWALR-NH$_2$ (SEQ ID NO:14), Ac-rlawsvaipaswrplpa-NH$_2$ (SEQ ID NO: 15), c(rlGwsvGipGswrplpa) (SEQ ID NO:20), c(rlGwsv-GipGswrplparlGwsvGipGswrplpa) (SEQ ID NO:21) and mixtures thereof.

In yet another aspect in the method for treating depression in an the analog of spadin or analog of propeptide spadin is Ac-rlGwsvGipGswrplpa-NH$_2$ (SEQ ID NO:4) or Ac-rlGws-vGipGswrplpaappppadlrdq-NH$_2$ (SEQ ID NO:9) or Ac-rlGwsvGipGswrplpa-NH$_2$ (SEQ ID NO:4) and Ac-rlGwsv-GipGswrplpaappppadlrdq-NH$_2$ (SEQ ID NO:9).

In the method for treating depression the pharmaceutically acceptable vehicle is selected from the group of distilled water, buffers, glycerol, polypropylene glycol, saline, phosphate buffered saline dextrose, ethanol, adjuvants and mixtures thereof. The adjuvants, are, for example, alum, aluminum phosphate, calcium phosphate, MPL™, CpG motifs, modified toxins, saponins, endogenous stimulatory adjuvants such as cytokines, Freunds complete and incomplete adjuvants, ISCOM type adjuvants, muramyl peptides and the like.

The analogs, as described herein, are present in the pharmaceutical compositions, as described herein, in an amount of 0.05 to 10 mg/kg or 0.01 1 to 3 mg/kg or 0.015 to 5 mg/kg.

In yet another embodiment the present invention provides a method for treating depression in an animal, said method comprising administering to said animal in need of said treatment the a pharmaceutically effective amount of a biodegradable pharmaceutical composition as described herein.

The present invention also provides a pharmaceutical composition, as described herein, or biodegradable pharmaceutical composition, as described herein, to treat depression or for the manufacture of a medicament to treat depression. This pharmaceutical composition is in a pharmaceutically effective amount to treat depression.

A method for blocking TREK-1 channel activity, said method comprising administering to an animal an effective amount of the composition, as described herein, or the pharmaceutical composition as described herein is another aspect of the invention.

A method for blocking TREK-1 channel activity, said method comprising administering to an animal an effective amount of the biodegradable pharmaceutical composition as described herein is another embodiment of the invention.

The invention will now be illustrated by the following description of examples which, of course, are not limiting in nature. Further characteristics of the invention will become clear from the following observations that are, of course, provided only by way of illustration and do not in any way limit the scope of the invention.

EXAMPLES

Example 1—Materials and Methods

Spadin Analogs

Spadin was synthesized by Gencust (France). All the other peptides (see FIG. 1) were synthesized by the American Peptide Company (Sunnyvale, Calif., USA). Peptides were purified by the supplier and had a purity of >80%. The purity was verified by analytical HPLC and mass spectral analysis.

With the aim to improve stability and/or duration of action and bioavailability of the spadin different analogs of spadin were synthesized. Peptide analogs were engineered from both spadin and PE sequences. To achieve this goal, longer or shorter spadin peptides were synthesized and also peptides were synthesized with the retro-inverso (ri) amino acid approach. This approach consists in synthesizing peptides in which not only the chirality of amino acid is inverted by replacing all L-amino acids by D-amino acids, but also the amino acid sequence is reversed (Bonny, C. et al. Cell-permeable peptide inhibitors of JNK: novel blockers of beta-cell death. Diabetes 50, 77, (2001); Chorev, M. et al.

Recent developments in retro peptides and proteins—an ongoing topochemical exploration. Trends Biotechnol 13, 438, (1995)). In such a way, the side chains of amino acids are in a very similar position to that of the native peptide (Bonny, C. et al. Cell-permeable peptide inhibitors of JNK: novel blockers of beta-cell death. Diabetes 50, 77, (2001); Chorev, M. et al. Recent developments in retro peptides and proteins—an ongoing topochemical exploration. Trends Biotechnol 13, 438, (1995); Van Regenmortel, M. H. et al. D-peptides as immunogens and diagnostic reagents. Curr Opin Biotechnol 9, 377, (1998)). Retro-inverso peptides are often more resistant to protease hydrolysis and have physiological activities closed and sometimes higher than the parent L-peptides (Taylor, M. et al. Development of a proteolytically stable retro-inverso peptide inhibitor of beta-amyloid oligomerization as a potential novel treatment for Alzheimer's disease. Biochemistry 49, 3261, (2010); Weeden, T. et al. A retro-inverso alpha-melanocyte stimulating hormone analog with MC1R-binding selectivity. J Pept Sci 17, 47, (2011)).

Sixteen spadin analogs for their ability to block TREK-1 channel activity were screened (see below). The two most efficient were retained for further studies using behavioral tests and their effects on neurogenesis. Because the activation of TREK-1 channels was shown to be beneficial in different pathologies such epilepsy or pain, the effects of analog treatments on these pathologies were studied.

Cell Culture of h-TREK-1/Cell Line

The human-TREK-1/HEK293 cell line (h-TREK-1/HEK) (Moha ou Maati, H. et al. (2011). *PloS one*, 6 (10), e25602) and HEK-IKS cell line (Ducroq, J. et al, (2010) Br J Pharmacol, 159(1):93-101) were grown in the presence of 0.5 mg/mL G418 in Dulbecco's modified Eagle's medium supplemented with 10% (v/v) heat inactivated fetal bovine serum containing 1% (v/v) penicillin/streptomycin in an atmosphere of 95% air/5% CO2.

HEK-293 native cells were grown in serum in an atmosphere of 95% air/5% $CO_2$ in Dulbecco's modified Eagle's medium supplemented with 10% (v/v) heat inactivated fetal bovine containing 1% (v/v) of penicillin/streptomycin and Glutamax×1. Cells were plated at a density of 20000 cells/35 mm dish and after 24 h cells were transfected using the JetPEI® method (Polyplus, France) with 25 ng/35 mm dish of p-IRES-HERG channel vector. Patch clamp experiments were carried out 48 h after transfection Animals Naïve male C57Bl/6J mice from 7 to 9 weeks old were used in all experiments (Janvier laboratory). Mice were housed 10 animals per cage under a 12-h light/12-h dark cycle (light on at 8:00 am), in a ventilated room at a temperature of 22±1° C. Animals had free access to water and food (A03; SAFE, Augy, France). All experiments were conducted according to policies on the care and use of laboratory animals of the Society for Neuroscience, and also with respect to national laws on animal use. The local Ethics Committee (CIEPAL) approved the experiments.

Treatments

Stock solutions were prepared of 2 mg/mL (10-3M) in distilled water, and before injection spadin solution was diluted in NaCl 0.9% to obtain the different concentrations used for treatments. Corticosterone (Sigma-Aldrich, France) was dissolved in drinking water at the concentration of 3.5 mg/L in the presence of 4.5 g/L of beta-cyclodextrin. The mixture was filled into opaque bottles to protect from the light and mice had a free access to this solution. Fluoxetine (Sigma-Aldrich, France) was dissolved in drinking water at the dose of 80 mg/L and administered during 21 days. For i.p. administration, fluoxetine (TEVA Santé, France) was dissolved in NaCl 0.9% at a concentration of 0.75 mg/mL. The amount injected was 3 mg/kg. Spadin and analogues were administered by i.v. injection. For acute treatment, drugs were administered in a single 100 µL bolus 30 min prior to the beginning of the behavioral tests. For subchronic treatment drugs were injected during 4 consecutive days and behavioral tests were performed on day 5, without additional injection.

Statistics

Data were expressed as mean±S.E.M. Statistical analysis of differences between groups was performed by using Mann-Whitney. In all analyses, the level of significance was set at $p<0.05$ (*), $p<0.01$ () and $p<0.001$ (*).

In the learned helplessness test latencies to escape were recorded for each of the 30 trials. The average value was calculated for each of the five trials, thus 6 blocks of values were obtained in addition to the overall average escape latency. A Mann-Whitney test was carried out on both overall latencies and blocks of trials.

Example 2—Electrophysiology

All electrophysiological experiments were performed on h-TREK-1/HEK cells seeded at a density of 20 000 cells/35-mm dish after 2-6 days of culture. All electrophysiological recordings were performed in whole cell configuration of the patch clamp technique. Each current was evaluated by using a RK 400 patch clamp amplifier (Axon Instrument, USA), low-pass filtered at 3 kHz and digitized at 10 kHz using a 12-bit analog-to-digital converter digidata (1322 series, Axon Instrument, USA). All current amplitudes are expressed in current densities. Results were expressed as mean±standard error of the mean (SEM). Patch clamp pipettes were pulled using a vertical puller (PC-10, Narishige) from borosilicate glass capillaries and had a resistance of 3-5 MΩ. The bath solution contained 150 mM NaCl, 5 mM KCl, 3 mM $MgCl_2$, 1 mM $CaCl_2$ and 10 mM HEPES adjusted to pH 7.4 with NaOH. The pipette solution contained 155 mM KCl, 3 mM $MgCl_2$, 5 mM EGTA and 10 mM HEPES adjusted to pH 7.2 with KOH. TREK-1 currents were evaluated in the presence of a cocktail of potassium channel inhibitors (K+ blockers: 3 mM 4-aminopyridine (4-AP), 10 mM tetraethylammonium (TEA), 10 µM glibenclamide, 100 nM apamin and 50 nM charybdotoxin). All experiments were performed at room temperature (21-22° c.). Stimulation protocols and data acquisition were carried out using a microcomputer (Dell Pentium) with a commercial software and hardware (pClamp 8.2). Currents were recorded by voltage clamp steps to membrane potentials of −100 to +60 mV in 20 mV steps applied from a holding potential of −80 mV. Duration of depolarization pulses were 0.825 ms, and the pulse cycling rate was 5 sec. TREK-1 current amplitudes were evaluated at the end of the stimulation pulses. Cells were continuously superfused with a microperfusion system. Inhibitory effects of spadin and analogs were performed on arachidonic acid pre-activated TREK-1 currents. Spadin and analogs were tested at the unique dose of 100 nM. For both Analog 3 (SEQ ID:4) and Analog 8 (SEQ ID:9) concentration-dependant inhibitions were performed by applying concentrations ranging between 1 nM to 1 µM. IKS currents were activated by voltage clamp steps of membrane potentials from −100 to +100 mV in 20 mV steps applied from a holding potential of −80 mV. Tail currents were generated by repolarization to −40 mV. Duration of both depolarization and repolarization pulses were 2.4 s, and the pulse cycling rate was 10 s. IKR currents were activated by voltage clamp steps of membrane potentials from −100 to +100 mV in 10 mV steps applied from a holding potential of +80 mV and tail currents were generated by a repolarization to +40 mV. Duration of both depolarization and repolarization pulses were 1 s, and the pulse cycling rate was 5 s. The amplitudes of IKS and IKR currents were calculated at both the end of the first pulse and the peak of the tail pulse.

In order to identify analogs having a better affinity for TREK-1 channels than spadin, their blockade effect on the activity of TREK-1 channels expressed in the h-TREK-1/HEK cell line (Moha ou Maati, H. et al. A human TREK-1/HEK cell line: a highly efficient screening tool for drug development in neurological diseases. PLoS One 6, e25602, (2011)) was first studied. TREK-1 channels expressed in this cell line have kept all their modulating properties (Moha ou Maati, H. et al. A human TREK-1/HEK cell line: a highly efficient screening tool for drug development in neurological diseases. PLoS One 6, e25602, (2011)). By using the whole cell configuration of the patch clamp technique, fifteen analogs, named Analog 2 (SEQ ID:3) to Analog 16 (SEQ ID:21) (FIG. 1 and FIG. 8) were tested at the unique concentration of 100 nM (n=10 to 12), SEQ ID:1, corresponding to the spadin, (Mazella, J. et al. Spadin, a sortilin-derived peptide, targeting rodent TREK-1 channels: a new concept in the antidepressant drug design. PLoS Biol 8, e1000355, (2010); Moha ou Maati, H. et al. A human TREK-1/HEK cell line: a highly efficient screening tool for drug development in neurological diseases. PLoS One 6, e25602, (2011); Moha Ou Maati, H. et al. Spadin as a new antidepressant: absence of TREK-1-related side effects. Neuropharmacology 62, 278, (2012)) was used as reference. The analogs correspond to the following SEQ ID Nos: analog 2 (SEQ ID NO:3), analog 3 (SEQ ID NO:4), analog 4 (SEQ ID NO:5), analog 5 (SEQ ID NO:6), analog 6 (SEQ ID NO:7), analog 7 (SEQ ID NO:8), analog 8 (SEQ ID NO:9), analog 9 (SEQ ID NO:10), analog 10 (SEQ ID NO:11), analog 11 (SEQ ID NO:12), analog 12 (SEQ ID NO:13), analog 13 (SEQ ID NO:14), analog 14 (SEQ ID NO:15), analog 15 (SEQ ID NO:20) and analog 16 (SEQ ID NO:21).

Figure 8:
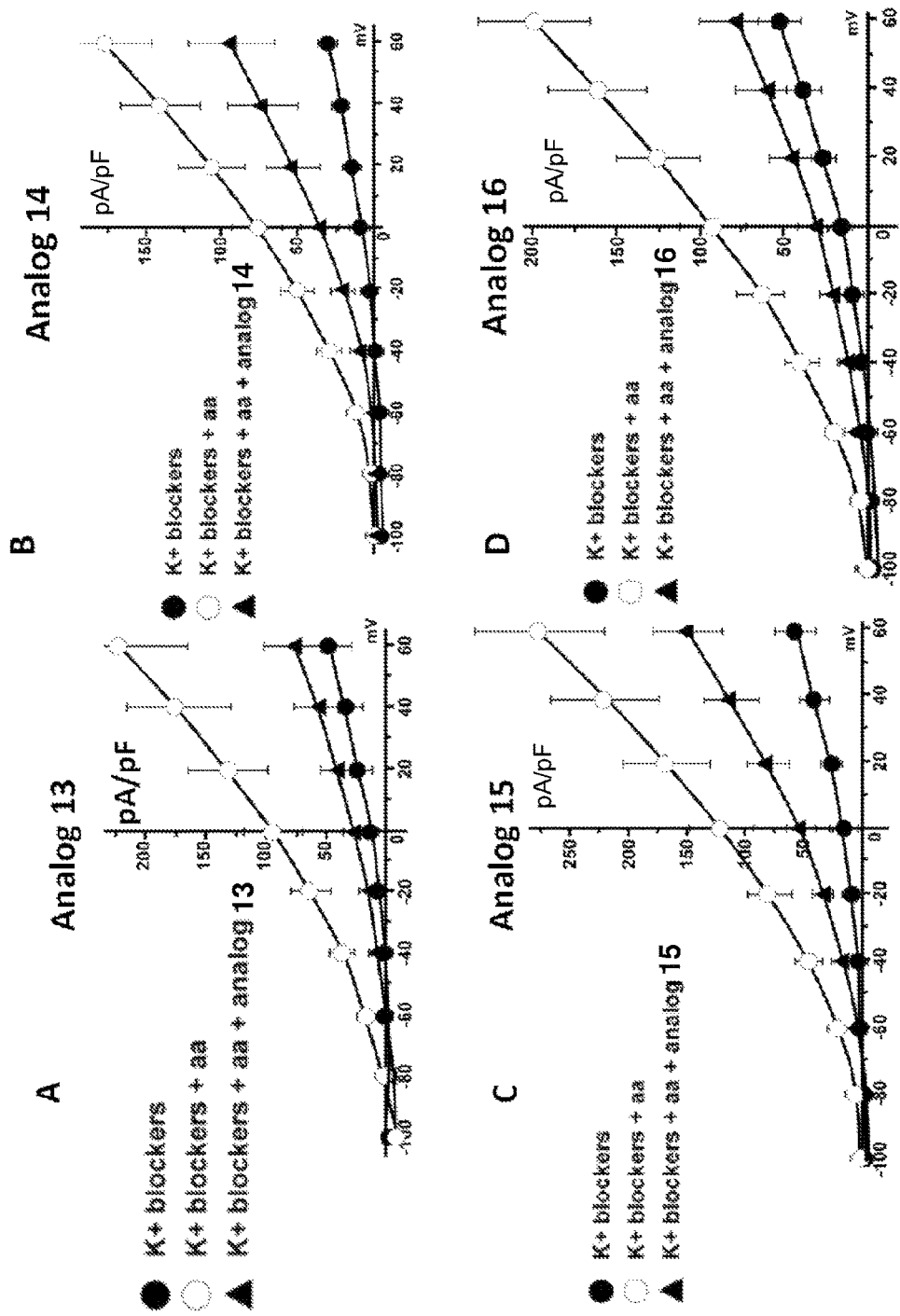
FIG. 8 (A to D) shows I=f(V) curves of analog 13 to 16. All experiments were performed as described in FIG. 2.
Figure 9:
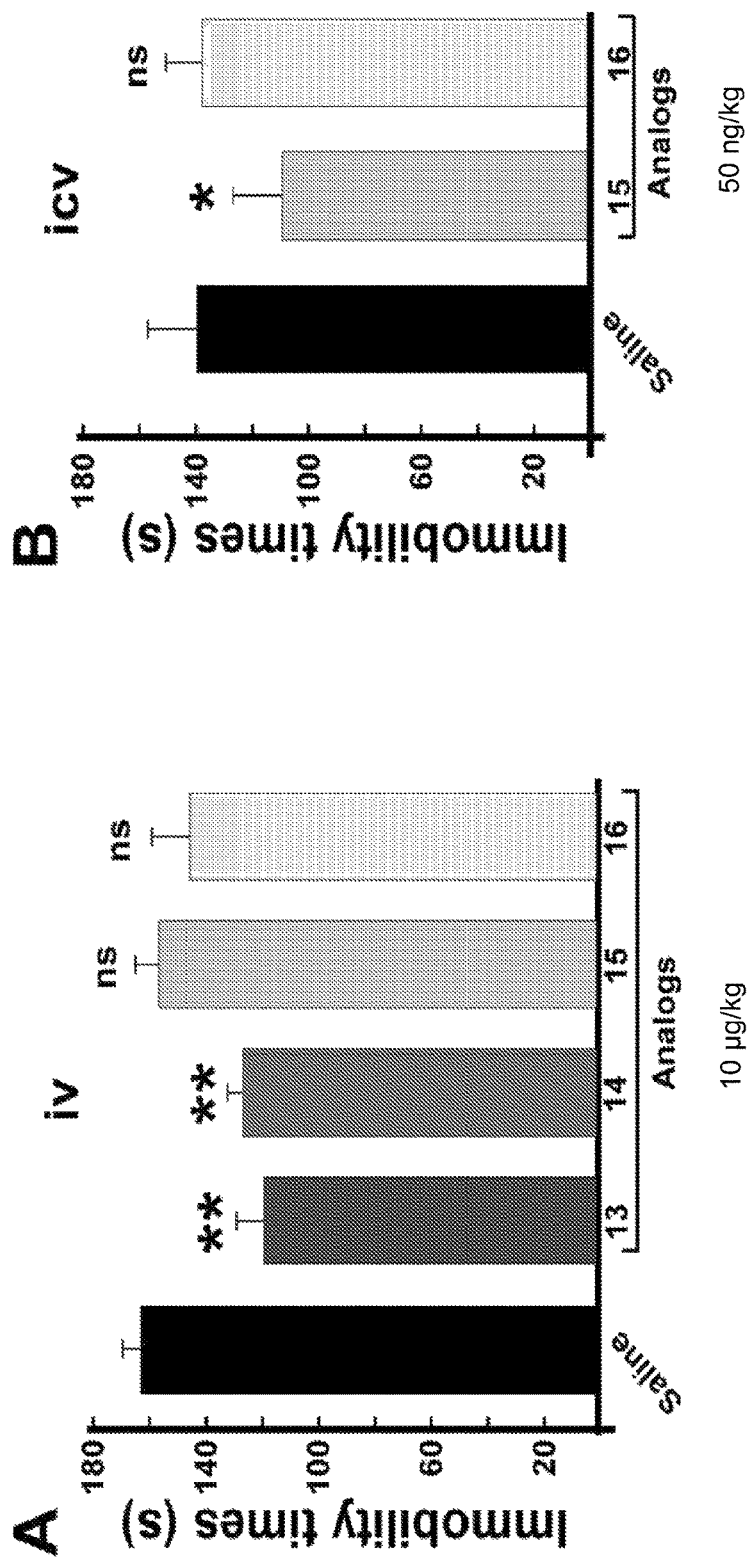
FIG. 9 are graphs (A to B) showing the results of a Forced Swimming Test (FST) performed after an acute treatment with analog 13 (SEQ ID NO:14), analog 14 (SEQ ID NO:15), analog 15 (SEQ ID NO:16) and analog 16 (SEQ ID NO:17). Immobility times were measured 30 minutes after the i.v. injection of the drugs at a dose of 1 μg/kg (FIG. 9A) in a single bolus of 100 μL of NaCl 0.9% or after the i.c.v. injection of the drugs at a dose of 50 ng/kg (FIG. 9B) in a single bolus of 5 μL of NaCl 0.9%.

This data indicated that only six analogs, Analog 3 (SEQ ID NO:4) and Analog 8 (SEQ ID NO:9) (FIG. 2) and Analog 13 (SEQ ID NO:14), Analog 14 (SEQ ID NO:15), Analog 15 (SEQ ID NO:20) and Analog 16 (SEQ ID NO:21) (FIG. 8), presented an increased blockade effect. Analog 2 (SEQ ID NO:3) corresponds to the N-terminal-acetylated and C-terminal amidated form of spadin. Analog 2 (SEQ ID NO:3) displayed very similar effects to those of spadin. IC50 values calculated from dose-response curves were of 11.5±0.59 and 9.95±0.85 for Analog 3 (SEQ ID NO:4) and Analog 8 (SEQ ID NO:9) respectively (FIG. 2C), these values have to be compared to 56.39±0.01 nM determined for spadin on the same cell line. Analog 2 (SEQ ID NO:3) had an IC50 of 60±0.41 nM (FIG. 2C). These data indicated that Analog 3 (SEQ ID NO:4) and Analog 8 (SEQ ID NO:9) have a 6-fold higher affinity for TREK-1 channels. Analog 13 (SEQ ID NO:14) had an IC50 of 40 pM, Analog 14 (SEQ ID NO:15) had an IC50 of 4 pM, Analog 15 (SEQ ID NO:20) had an IC50 of 40 pM and Analog 16 (SEQ ID NO:21) had an IC50 of 1 pM (FIG. 8F). These analogs were used for investigating antidepressant properties.

Example 3—Behavioral Tests

Behavioral experiments were performed with naïve mice. The experimenter was blind to experimental groups. All mice were naïve to every behavioral test used.

Example 3A—Forced Swimming Test (FST)

The animals were individually placed in a non-escapable cylinder (height 30 cm, diameter 15 cm) filled with 15 cm-water at 22±1° C. The trial was conducted for 6 min. The total period of immobility was manually measured during the last 4 min of the test. A mouse was considered immobile when it remained floating with only slight movements to keep its head above water.

The antidepressant effects of both analogs were first studied after an acute injection in the Forced Swim Test (Mazella, J. et al. Spadin, a sortilin-derived peptide, targeting rodent TREK-1 channels: a new concept in the antidepressant drug design. PLoS Biol 8, e1000355, (2010)) The main goal of this study was to find a molecule that can be used in human clinic and thus remained active after several days of administration. Consequently, this study was pursued after a sub-chronic administration of both analogs.

Figure 3:
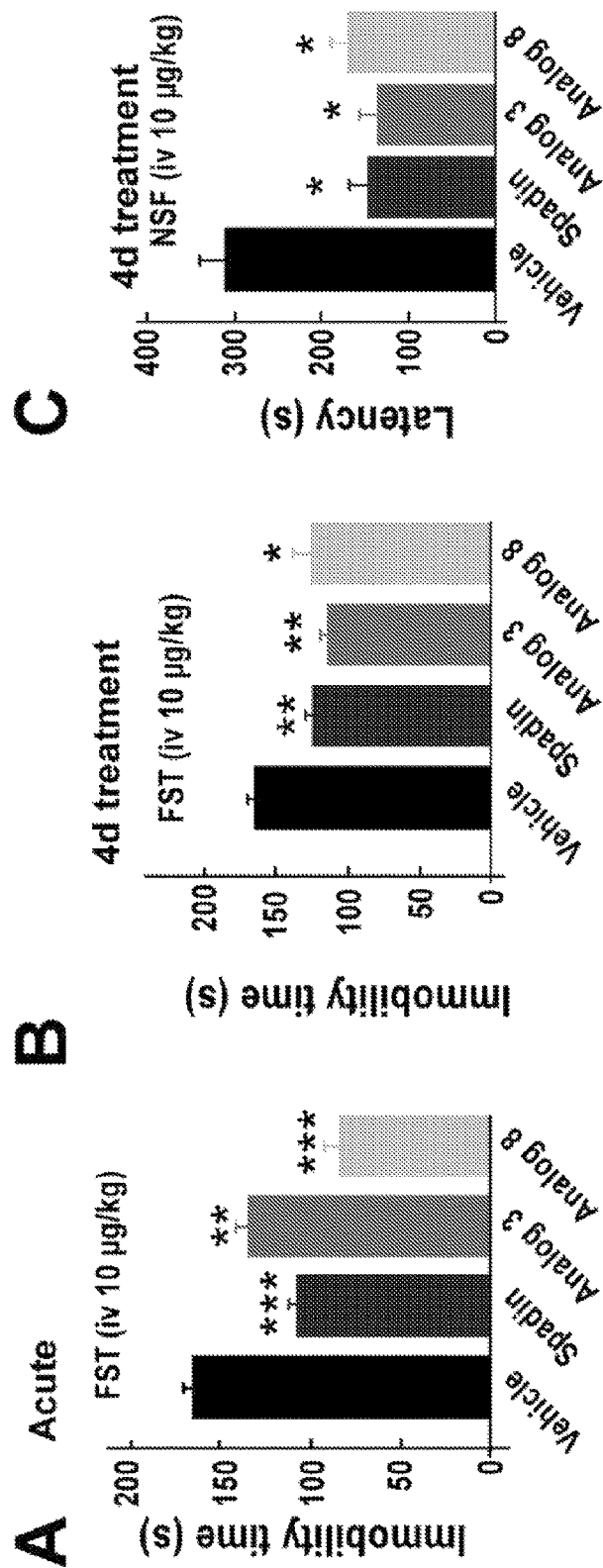
FIG. 3 are graphs (A to D) and a curve (E) showing Behavioral tests with spadin, Analog 3 (SEQ ID NO:4) and Analog 8 (SEQ ID NO:9).

Here again, regular spadin was used as control. A 10 μg/kg acute intravenous (i.v.) injection of spadin or both Analog 3 (SEQ ID NO:4) and Analog 8 (SEQ ID NO:9) significantly reduced the immobility time of mice compared to saline injected mice (FIG. 3A). Values were 166.13±5.54 sec, 107.40±5.05 sec, 135.10±8.11 sec and 83.60±9.01 sec for saline, spadin (U=0, p<0.001), Analog 3 (SEQ ID NO:4) (U=8, p=0.01) and Analog 8 (SEQ ID NO:9) (U=0, p=0.001) respectively (n=10 for each group). These results showed an antidepressant effect of spadin's analogs after an acute treatment.

In the FST, subchronic treatments of 4 days (10 μg/kg i.v. injected once a day) with spadin or analogs induced a significant decrease of the immobility times. Immobility time observed were of 161.80±8.12 sec, 123.70±7.16 sec (U=10.5, p<0.01), 114.9±9.82 sec (U=10.5, p<0.01), 124.1±10.53 sec (U=17.5, p<0.05) for saline solution, spadin, Analog 3 (SEQ ID NO:4) and Analog 8 (SEQ ID NO:9), respectively (FIG. 3B). This data clearly indicated that analogs are efficient even after four days of treatment and that an antidepressant effect of spadin's analogs was achieved after a subchronic treatment.

For improving the spadin efficacy, in addition to an increased affinity, analogs have to be more stable when injected in vivo Measured with the FST seven hours after the injection, the remaining efficiency of spadin was only 30% of the initial efficacy whereas it was 84% at 3 h and after 17 h there was no reduction in the immobility times. Times of immobility were of 170.3±4.5 sec, 102.4±6.2 sec (U=0, p<0.001), 113.2±5.0 sec (U=0, p<0.001), 150.8±6.5 sec (U=19, p<0.05) and 175.3±7.5 sec (FIG. 4A). These data indicated that the stability and/or duration of action of this dose of spadin is around 6 hours.

To investigate this property, both analogs were i.v. injected and mice were tested in the FST. For each analog, at different times after the injection, 1, 3, 7, 12, 16 and 24 hours, 10 naïve animals were tested. Saline injected animals were only tested at 1 and 24 hours. It appeared that both analogs have kept their ability to reduce the immobility times after 16 hours. The immobility times were very similar between 1 hour and 16 hours 123.4±7.0 sec and 129.6±12.7 sec, and 121.7±5.2 sec and 129.1±12.0 sec for Analog 3 (SEQ ID NO:4) and Analog 8 (SEQ ID NO:9), respectively (FIG. 4B). The mean value for saline treated animals was of 162.7±4.7 sec (FIG. 4B) These data clearly indicated that both analogs have a longer in vivo stability and/or duration of action when compared to spadin.

Analog 13 (SEQ ID NO:14) and Analog 14 (SEQ ID NO:15) showed also strong activity after i.v. injection while Analog 15 (SEQ ID NO:20) and Analog 16 (SEQ ID NO:21) did not. However, Analog 15 (SEQ ID NO:20) was active by i.c.v injection while Analog 16 (SEQ ID NO:21) was not.

Example 3B—Novelty Suppressed Feeding (NSF)

The NSF paradigm is a two day test protocol. Day one, mice were deprived from food. Day two mice were placed in a highly brightly lit area, in a plastic box (45×45×20 cm), with a floor covered with wooden bedding. The test was carried out during a 10 min period; during this time the latency to eat was measured. During the test a single pellet of food was placed in the center of the box, on a white platform.

Similar results were obtained, as in the FST using subchronic treatment, in the novelty suppressed feeding test. Spadin and both analogs reduced the latency to feed. Values were of 305.00±62.47 sec, 151.11±17.70 sec (U=13, p<0.05), 143.88±23.42 (U=11, p<0.05) and 167.00±22.96 (U=13, p<0.05) for saline solution, spadin, Analog 3 (SEQ ID NO:4) and Analog 8 (SEQ ID NO:9), respectively (FIG. 3C).

Example 3C Learned Helplesness (LH)

The learned helplessness test is divided in a 4 day training session and one day test session.

During the training session mice were exposed to 360 inescapable 2 sec foot shocks, with an inter trial interval of 8 sec. A non shocked group was exposed to the apparatus for the same duration but no shock was delivered.

The test consisted in 30 trials separated by a 30 sec interval. One trial was defined as a 5 sec period before shock onset and was terminated when the mouse moved to the second compartment or at the end of the shock onset. During the test, the latency to escape for each mouse during every trial was recorded.

Example 3D—Tail-Immersion Test

Mice were i.v. injected with 10 µg/kg of spadin in a bolus of 100 µL or 100 µL of a saline solution (0.9% NaCl) 30 min before the beginning of the test. The tail was immersed in a water bath at 48° C. until withdrawal was observed (cut-off time: 30 s). Two separate withdrawal latency time determinations were averaged.

Figure 6:
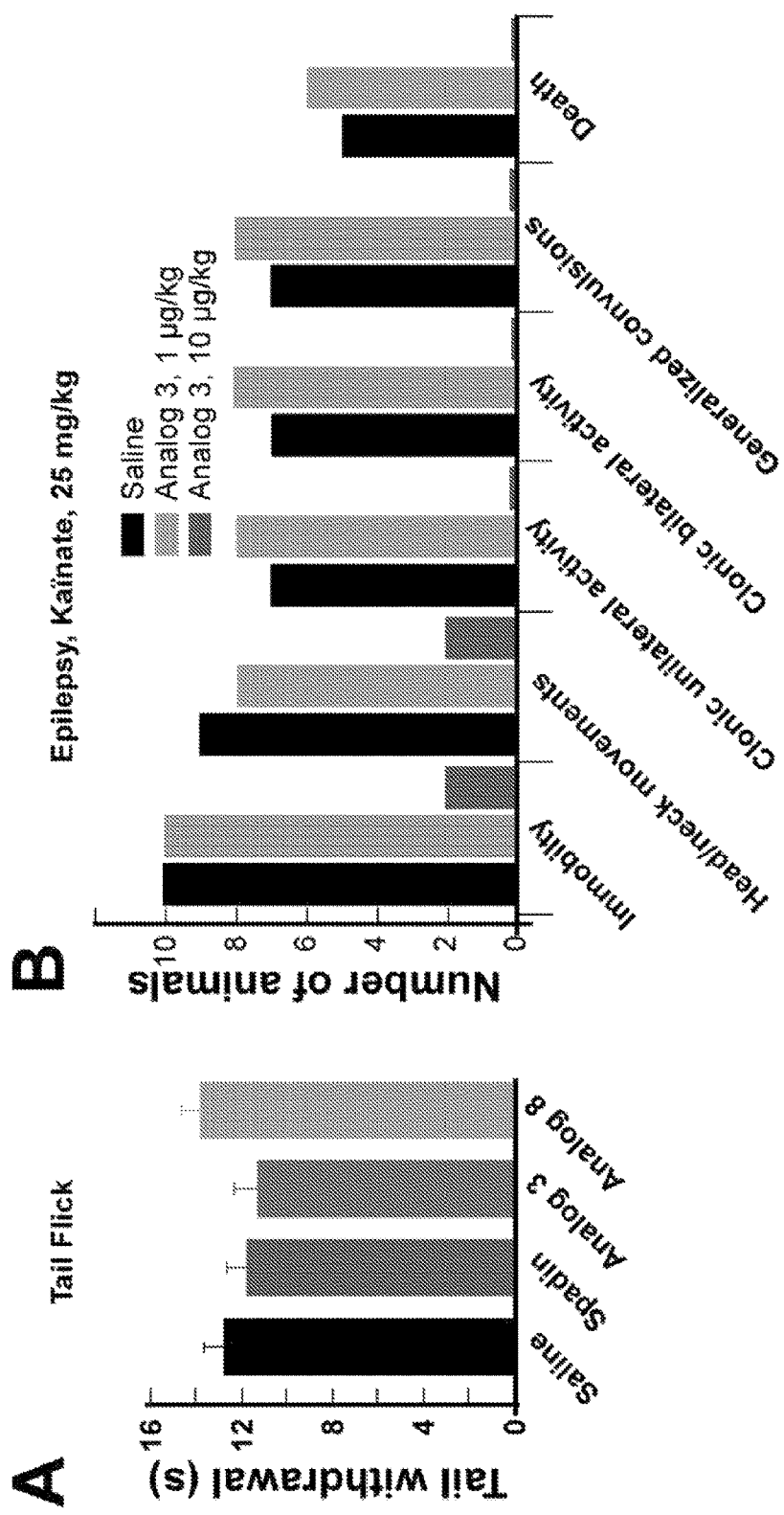
FIG. 6. are grafts and curves showing side effects.
Figure 7:
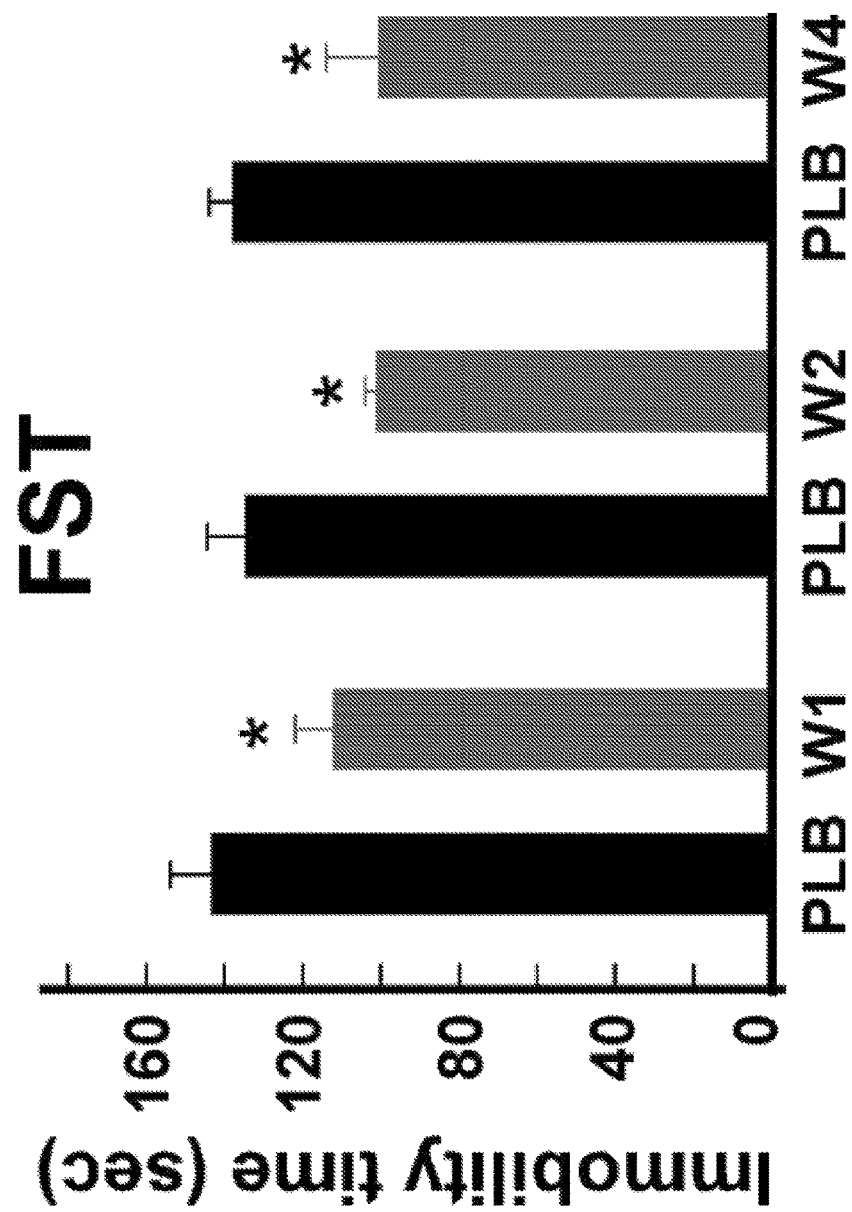
FIG. 7 is a graph showing the effects of long term treatments with spadin. Spadin-MedinGel (W) formulation and placebo-Medingel (PLB) were subcutaneously injected in the neck of mice. Immobility times were measured in a Forced Swimming Test (FST) at one, two or four weeks (W1, W2, W4) after injection. For each week values obtained with formulations were compared with their corresponding placebo values by using the Mann-Whitney test. PLB, placebo, *, p<0.05.

This test was used to check whether or not these analogs induced side effects. First and because TREK-1 channels are involved in thermal pain, we analyzed the effects of both Analog 3 (SEQ ID NO:4) and Analog 8 (SEQ ID NO:9) on thermal pain by the way of tail immersion test. It clearly appeared that analogs and spadin did not increase the thermal pain sensation (FIG. 6A). Measured tail withdrawal times were of 12.75±0.96 sec, 11.79±0.89 sec, 11.32±1.04 sec and 13.85±0.72 sec for saline, spadin, Analog 3 (SEQ ID NO:4) and Analog 8 (SEQ ID NO:9), respectively (FIG. 6A).

Because both analogs displayed the same properties and the same efficacy in behavioral tests it was decided to focalize on Analog 3 (SEQ ID NO:4). This choice was supported by the fact that Analog 3 (SEQ ID NO:4) is the retro-inverso of spadin and consequently shorter than Analog 8 (SEQ ID NO:9). Moreover, Analog 3 (SEQ ID NO:4) seemed to be active for longer duration in vivo (see FIG. 4B) than Analog 8 (SEQ ID NO:9).

Example 3E—Seizure Induced by Kainate

Kainate solutions were prepared in a solution of 140 mM NaCl (saline solution). Spadin 10 µg/kg or vehicle were i.v. injected and immediately after the injection kainate, 25 mg/kg i.p injected in a bolus of 100 µL. Mice (n=10 per group) were monitored during 2 h for onset and extent of seizures. Six levels of seizure severity were defined as follows: 1—immobility, 2—head/neck movements, 3—clonic unilateral activity, 4—clonic bilateral activity, 5—generalized convulsions, and 6—death. Seizure severity was blindly scored (Moha ou Maati, H. et al. A human TREK-1/HEK cell line: a highly efficient screening tool for drug development in neurological diseases. PLoS One 6, e25602, (2011)). The seizure index was calculated by averaging the points for seizure activity in each group (n=10 per treatment).

TREK-1 channel activation is also involved in the protection against epilepsy. Analog 3 (SEQ ID NO:4) at a dose of 10 µg/Kg i.v. was injected, had an important protective effect against epilepsy seizure triggered by kainate injections at a dose of 25 mg/Kg in a bolus of 100 µL. Only two mice among 10 injected with both kainate and Analog 3 (SEQ ID NO:4) reached the two less severe stages of the epilepsy seizures, immobility and head or neck movements. No other stages of epilepsy were observed for Analog 3 (SEQ ID NO:4) injected mice. At least 9 among 10 saline injected mice have reached the two first stages and five of them died (FIG. 6B). The effect of Analog 3 (SEQ ID NO:4) was dose-dependent since a dose of 1 µg/Kg showed no protective effect (FIG. 6B).

Example 4—Neurogenesis

One day after the injections of 5-bromo-2-deoxyuridine (BrdU), 12 mg per animal divided in four bolus of 100 µl injected every two hours with spadin or Analog 3 (SEQ ID NO:4) and Analog 8 (SEQ ID NO:9), mice were anesthetized with isoflurane and transcardially perfused with 20 mL of 0.9% NaCl followed by 20 mL paraformaldehyde in 4%/NaCl at a concentration of 0.9%. By using a vibratome (Leica) brains were cut in 40 µm sections, throughout the entire hippocampus. Eight slices, from bregma 3.3 to bregma 5.3, were retained to process the BrdU immunohistochemistry as previously described (Heurteaux, C. et al. Deletion of the background potassium channel TREK-1 results in a depression-resistant phenotype. Nat Neurosci 9, 1134, (2006)). For each BrdU labeling, slices were first incubated with a mouse monoclonal anti-BrdU antibody (1/8000, Becton Dinckinson). For chromogenic immunodetection, sections were then incubated for 2 hours in biotin-conjugated species specific secondary antibodies (1/400; Vector laboratories) followed by a peroxidase-avidin complex solution, to amplify the reaction. The peroxidase activity of immune complex was visualized with 3-3'diaminobenzidine (DAB) staining using the VectaStain ABC kit according to the manufacturer's protocol (Vector Laboratories).

Figure 5:
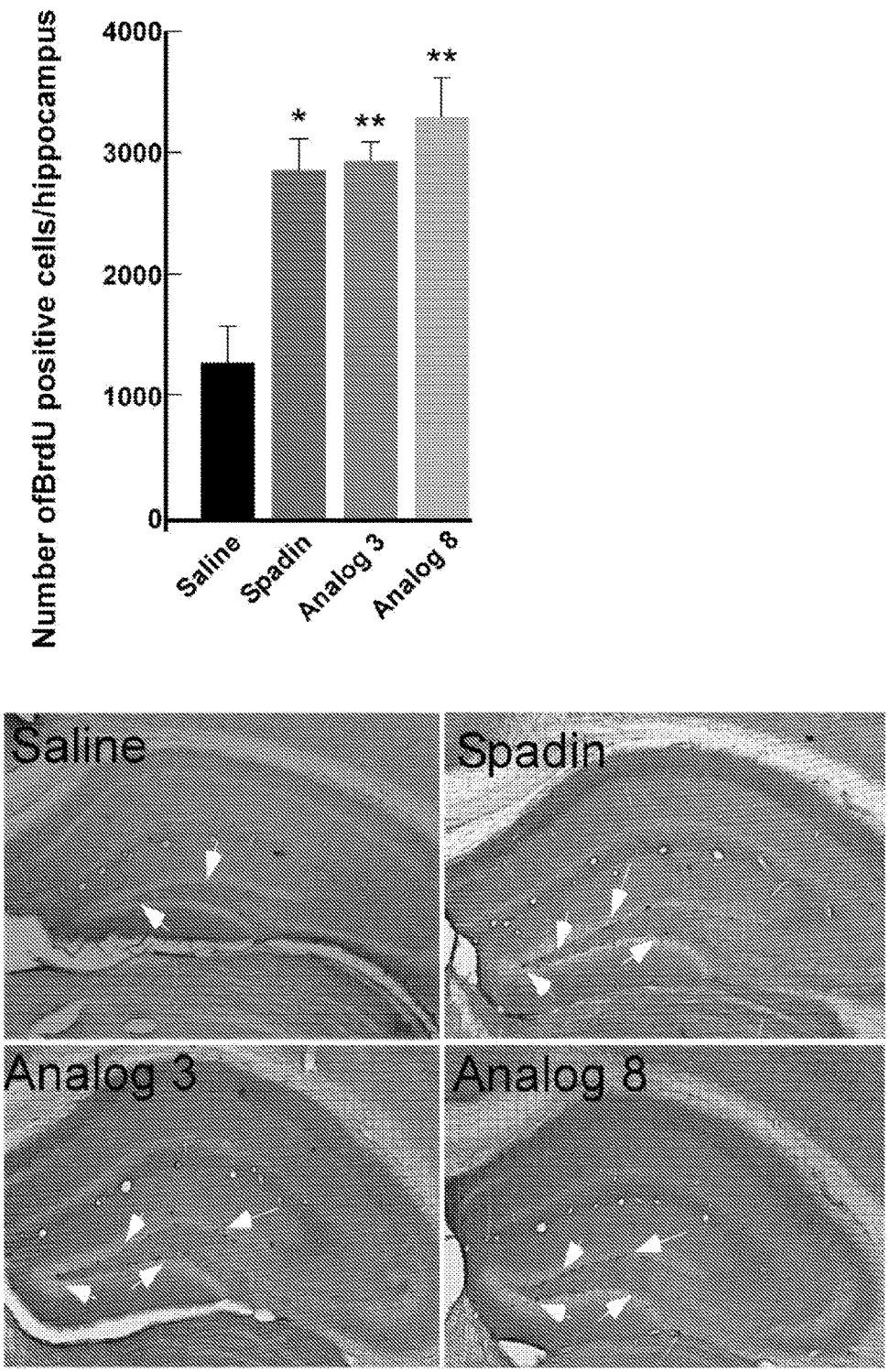
FIG. 5 are experiments showing results of neurogenesis.

It was previously shown that a 4-days subchronic treatment with spadin increased the hippocampal neurogenesis (Mazella, J. et al. Spadin, a sortilin-derived peptide, targeting rodent TREK-1 channels: a new concept in the antidepressant drug design. PLoS Biol 8, e1000355, (2010)). The ability of both analogs to induce a neoneurogenesis in the hippocampus was investigated. The neurogenesis in the dentate gyrus of the mouse hippocampus was analyzed by counting the number of progenitor cells that incorporated the DNA synthesis marker 5-bromo-2'deoxyuridine (BrdU). In the subgranular zone (SGZ), a 4 day treatment with spadin or analogs significantly increased the number of BrdU-positive cells when compared to saline conditions (FIG. 5A,B).

These data indicated that both analogs have conserved the ability to induce neurogenesis as observed for spadin but also for SSRIs or tricyclics.

Example 5—Side Effects on Cardiac Repolarizing Currents

It was also very important to check that Analog 3 (SEQ ID NO:4) as spadin is without effect on the two main repolarizing currents at the cardiac level, the fast component IKr and the slow component IKs. These channels are very important because they are responsible for the torsades de pointe which can lead to death. One of the more important side effects of antidepressant molecules is to induce torsades de pointe.

The current densities measured for $I_{Kr}$ at 0 mV were at the end of first pulse 225.14±33.09 pA/pF (n=5) and 224.48±35.94 pA/pF (n=5) in the absence or the presence of Analog 3 (SEQ ID NO:4), respectively (FIG. 6C). At the same potential, tail current densities in the absence or in the presence of Analog 3 (SEQ ID NO:4) were 204.59±34.18 pA/pF (n=5) and 212.99±38.38 pA/pF (n=5), respectively (FIG. 6C). IKs density currents measured at 0 mV are also very close. At the end of pulses these values were of 17.65±3.84 pA/pF (n=5) and 17.58±4.03 pA/pF (n=5) in the absence or the presence of Analog 3 (SEQ ID NO:4), respectively (FIG. 6D). IKS tail current densities were of 8.33±1.78 pA/pF (n=5) and 8.33±2.06 pA/pF (n=5), in the absence or in the presence of Analog 3 (SEQ ID NO:4), respectively (FIG. 6D).

Analog 3 (SEQ ID NO:4) did not modify currents generated either by IKr or IKS channels expressed in HEK cells (FIG. 6C,D).

Example 6—Chronic Treatment

Chronic treatments were achieved using long-acting formulations based on PLA/PEG copolymer. The formulations described herein were based on organic solution of polymers containing as the drug either Spadin (SEQ ID NO:1) or Analog 3 (SEQ ID NO:4). Typically, 0.4 grams of polymers, corresponding to a mix of a diblock copolymer and a triblock copolymer in defined mass ratio, were dissolved in 0.59 grams of a biocompatible solvent at room temperature overnight under constant magnetic stirring. The solvent was either a single solvent or a combination of solvents. The next day, 1-10 mg of drug was added to the polymer solution and stirred until complete dissolution. The formulations were loaded in a syringe before use. The composition of the formulations of Spadin and Analog 3 (SEQ ID NO:4) are shown in Table 1.

TABLE 1 composition of long-acting formulations

| Exp n° | Drug type | Drug loading % (w/w) | Polymer % (w/w) | % Polymer 1 | Polymer 1 code | Batch number | PEG (kDa) | Ratio (LA/EO) | DP-PEG |
|---|---|---|---|---|---|---|---|---|---|
| 2 | SEQ ID: 1 | 1.0% | 40% | 8% | P3R1 | MIC066 | 3 | 1.0 | 88 |
| 3 | SEQ ID: 1 | 1.0% | 40% | 8% | P6R1 | MIC064 | 6 | 1.0 | 136 |
| 4 | SEQ ID: 1 | 1.0% | 40% | 8% | P3R1 | MIC086 | 3 | 1.0 | 68 |
| 5 | SEQ ID: 1 | 1.0% | 40% | 8% | P6R1 | MIC084 | 6 | 1.0 | 136 |
| 6 | SEQ ID: 1 | 1.0% | 40% | 8% | P3R1 | MIC068 | 3 | 1.0 | 68 |
| 7 | SEQ ID: 1 | 1.0% | 40% | 8% | P6R1 | MIC084 | 6 | 1.0 | 136 |
| 8 | SEQ ID: 1 | 0.2% | 40% | 8% | P6R1 | MIC147-B | 6 | 1.0 | 136 |
| 9 | SEQ ID: 1 | 0.2% | 40% | 8% | P3R1 | MIC112 | 3 | 1.0 | 68 |
| 10 | SEQ ID: 1 | 0.6% | 40% | 8% | P3R1 | MIC112 | 3 | 1.0 | 68 |
| 11 | SEQ ID: 1 | 1.0% | 40% | 8% | P6R1 | MIC147-B | 6 | 1.0 | 136 |
| 12 | SEQ ID: 1 | 1.0% | 40% | 8% | P1R3.5 | MIC175-C | 1 | 3.5 | 23 |
| 13 | SEQ ID: 1 | 1.0% | 50% | 10% | P6R1 | MIC147-B | 6 | 1.0 | 136 |
| 14 | SEQ ID: 1 | 1.0% | 50% | 10% | P1R3.5 | MIC175-C | 1 | 3.5 | 23 |
| 19 | SEQ ID: 1 | 0.6% | 40% | 8% | P6R1 | MIC147-B | 6 | 0.9 | 136 |
| 20 | SEQ ID: 4 | 0.6% | 40% | 8% | P6R1 | MIC147-B | 6 | 0.9 | 136 |
| 21 | SEQ ID: 4 | 0.6% | 40% | 8% | P6R2 | MIC241-C | 6 | 2.06 | 136 |
| 22 | SEQ ID: 4 | 0.6% | 40% | 8% | P1R4 | MIC243-C | 1 | 3.99 | 23 |
| 23 | SEQ ID: 4 | 0.6% | 40% | 8% | P1R4 | MIC243-C | 1 | 3.99 | 23 |
| 24 | SEQ ID: 4 | 0.6% | 40% | 8% | P0.6R4 | MIC184-C | 0.6 | 4.16 | 14 |
| 25 | SEQ ID: 4 | 0.6% | 40% | 8% | P2R2 | MIC230 | 2 | 2.42 | 45 |
| 26 | SEQ ID: 4 | 0.6% | 40% | 8% | P2R2 | MIC230 | 2 | 2.42 | 45 |
| 27 | SEQ ID: 4 | 0.6% | 40% | 8% | P0.6R4 | MIC184-C | 0.6 | 4.16 | 14 |

| Exp n° | DP-PLA | % Polymer 2 | Polymer 2 code | Batch number | PEG (kDa) | Ratio (LA/EO) | DP-PEG | DP-PLA | Solvent | % Solvent (w/w) |
|---|---|---|---|---|---|---|---|---|---|---|
| 2 | 68 | 32% | P2R2D | MIC105 | 2 | 2.4 | 45 | 109 | DMSO | 59.0% |
| 3 | 136 | 32% | P2R2D | MIC106 | 2 | 2.4 | 45 | 109 | DMSO | 59.0% |
| 4 | 68 | 32% | P2R3D | MIC088 | 2 | 3.2 | 45 | 143 | DMSO | 59.0% |
| 5 | 136 | 32% | P2R3D | MIC086 | 2 | 3.2 | 45 | 143 | DMSO | 59.0% |
| 6 | 80 | 32% | P2R4D | MIC107 | 2 | 4.4 | 45 | 200 | DMSO | 59.0% |
| 7 | 136 | 32% | P2R4D | MIC107 | 2 | 4.4 | 45 | 200 | DMSO | 59.0% |
| 8 | 136 | 32% | P2R3D | MIC122 | 2 | 3 | 45 | 136 | DMSO | 59.8% |
| 9 | 80 | 32% | P2R4D | MIC130-1 | 2 | 4.1 | 45 | 136 | DMSO | 59.8% |
| 10 | 68 | 32% | P2R4D | MIC130-1 | 2 | 4.1 | 45 | 186 | DMSO | 59.4% |
| 11 | 136 | 32% | P2R3D | MIC122 | 2 | 3 | 45 | 136 | DMSO | 59.0% |

TABLE 1-continued composition of long-acting formulations

| 12 | 80  | 32% | P1R3.4D   | MIC-172-C | 1    | 3.4  | 23 | 77  | DMSO | 59.0% |
|----|-----|-----|-----------|-----------|------|------|----|-----|------|-------|
| 13 | 136 | 40% | P2R3D     | MIC122    | 2    | 3    | 45 | 136 | DMSO | 49.0% |
| 14 | 80  | 40% | P1R3.4D   | MIC-172-C | 1    | 3.4  | 23 | 77  | DMSO | 49.0% |
| 19 | 123 | 32% | P2R3D     | MIC259-C  | 2    | 2.43 | 45 | 110 | DMSO | 59.4% |
| 20 | 123 | 32% | P2R3D     | MIC259-C  | 2    | 2.43 | 45 | 110 | DMSO | 59.4% |
| 21 | 281 | 32% | P2R4D     | MIC242-C  | 2    | 4.14 | 45 | 188 | DMSO | 59.4% |
| 22 | 91  | 32% | P1R4D     | MIC225-C  | 1    | 3.85 | 23 | 80  | DMSO | 59.4% |
| 23 | 91  | 32% | P0.75R4D  | MIC208-C  | 0.75 | 4.37 | 17 | 74  | DMSO | 59.4% |
| 24 | 57  | 32% | P1R4D     | MIC229-C  | 1    | 3.85 | 28 | 88  | DMSO | 59.4% |
| 25 | 110 | 32% | P0.75R4D  | MIC206-C  | 0.75 | 4.37 | 17 | 74  | DMSO | 59.4% |
| 26 | 110 | 32% | P1R4D     | MIC225-C  | 1    | 3.85 | 23 | 88  | DMSO | 59.4% |
| 27 | 57  | 32% | P1R4D     | MIC226-C  | 1    | 3.85 | 23 | 88  | DMSO | 59.4% |

Figure 10:
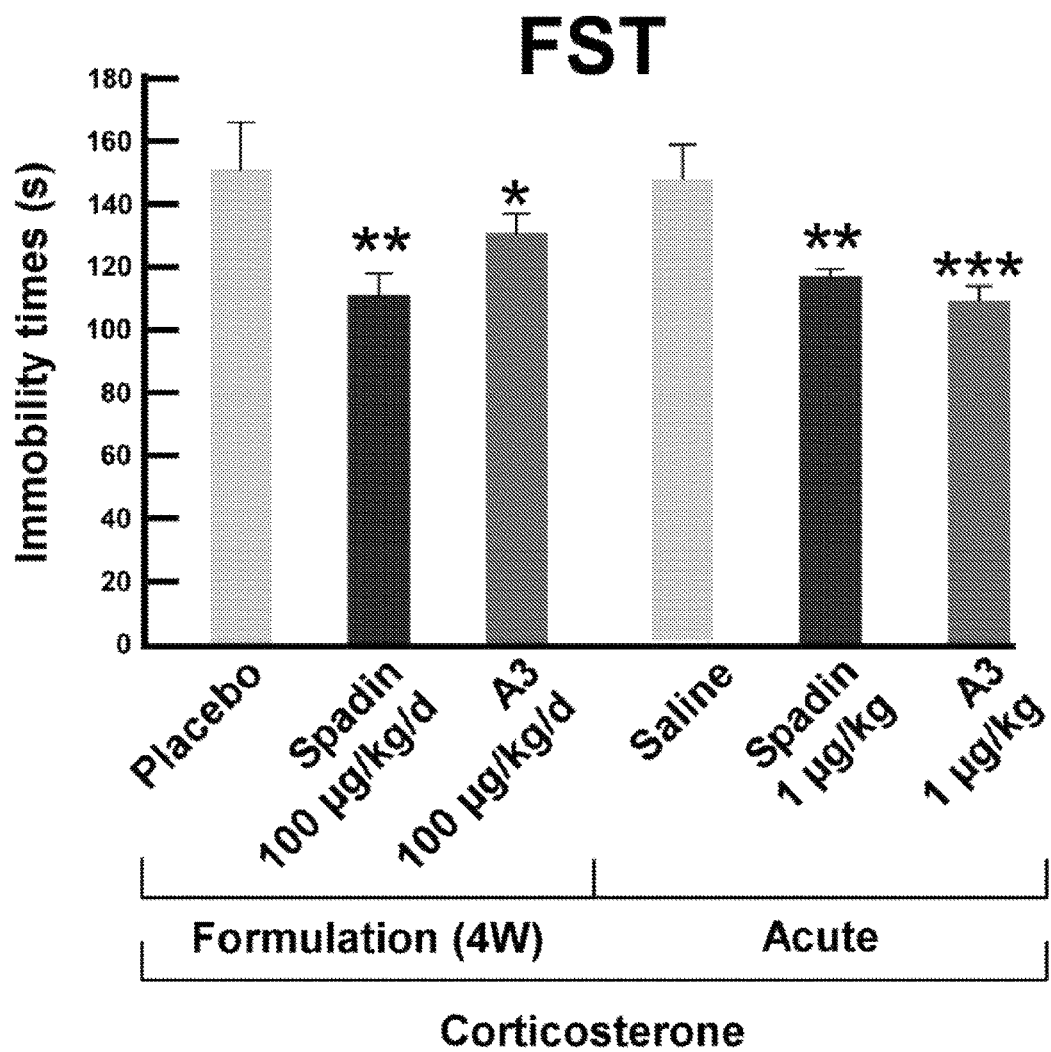
FIG. 10 is a graph showing the results of a Forced Swimming Test (FST) after long term treatment or after a sub-chronic treatment (4 days, 4 d) of Spadin and analog 3 in mice treated by Corticosterone. Mice were treated for 7 weeks by Corticosterone in their drinking water. Three weeks after the beginning of the treatment, mice in the formulation group were subcutaneously injected in the neck with long-acting formulations. Mice in the sub-chronic group were treated by i.v. injection of the drugs at a dose of 10 μg/kg during the four last days of the $7^{th}$ week of the Corticosterone treatment.
Figure 11:
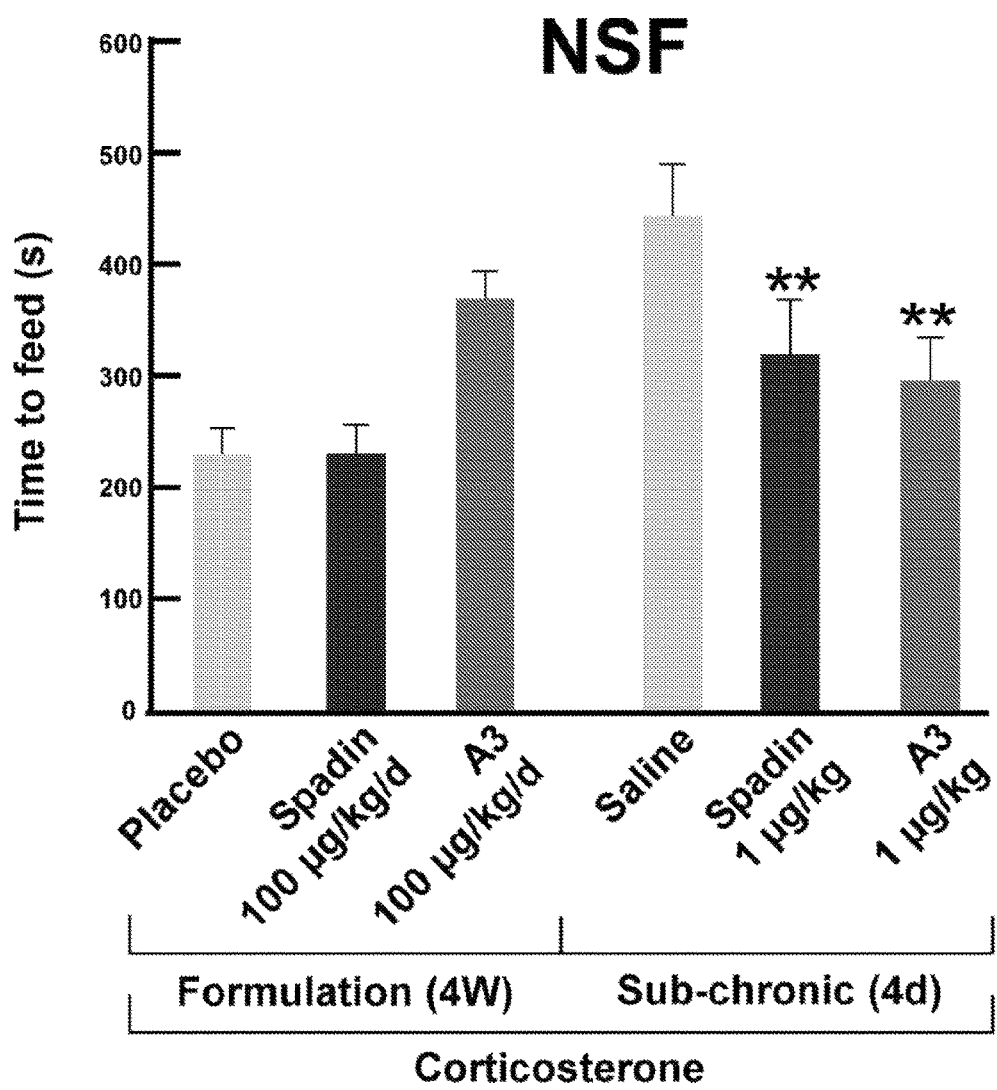
FIG. 11 is a graph showing the results of a Novelty Suppressed Feeding test (NSF) after long term treatment or after a sub-chronic treatment (4 days, 4 d) of Spadin and analog 3 in mice treated by Corticosterone. Mice were treated for 7 weeks by Corticosterone in their drinking water. Three weeks after the beginning of the treatment, mice in the formulation group were subcutaneously injected in the neck with long-acting formulations. Mice in the sub-chronic group were treated by i.v. injection of the drugs at a dose of 10 μg/kg during the four last days of the $7^{th}$ week of the Corticosterone treatment.

The formulation no 27 was selected for its optimal in vitro release profile and was adjusted for releasing 10 μg of Analog 3 (SEQ ID NO:4)/kg/day. The efficacy of formulation 27 was measured by FST after one, two and four weeks. At each time, tested mice are all naïve for the test. Mice injected with formulation 27 showed a significant reduction of immobility times. After one week the immobility times measured were 134.40±10.45 sec vs 112.00±9.31 sec (U=21.5, p<0.05) for the placebo-injected and Analog 3 (SEQ ID NO:4) formulation injected mice, respectively. After two weeks the immobility values were 133.80±11.03 sec vs 99.60±4.92 sec (U=17.5, p<0.05) for the placebo-injected and Analog 3 (SEQ ID NO:4) formulation injected mice, respectively. Interestingly, Analog 3 (SEQ ID NO:4) released by the MedinGel formulation was still active after 4 weeks, 137.20±6.93 sec vs 101.10±14.05 sec (U=20, p<0.05) for the placebo-injected and Analog 3 (SEQ ID NO:4) formulation injected mice, respectively. This result was confirmed in mice pretreated with Corticosterone in FST and NSF (FIG. 10 and FIG. 11 respectively)

DISCUSSION

Figure 4:
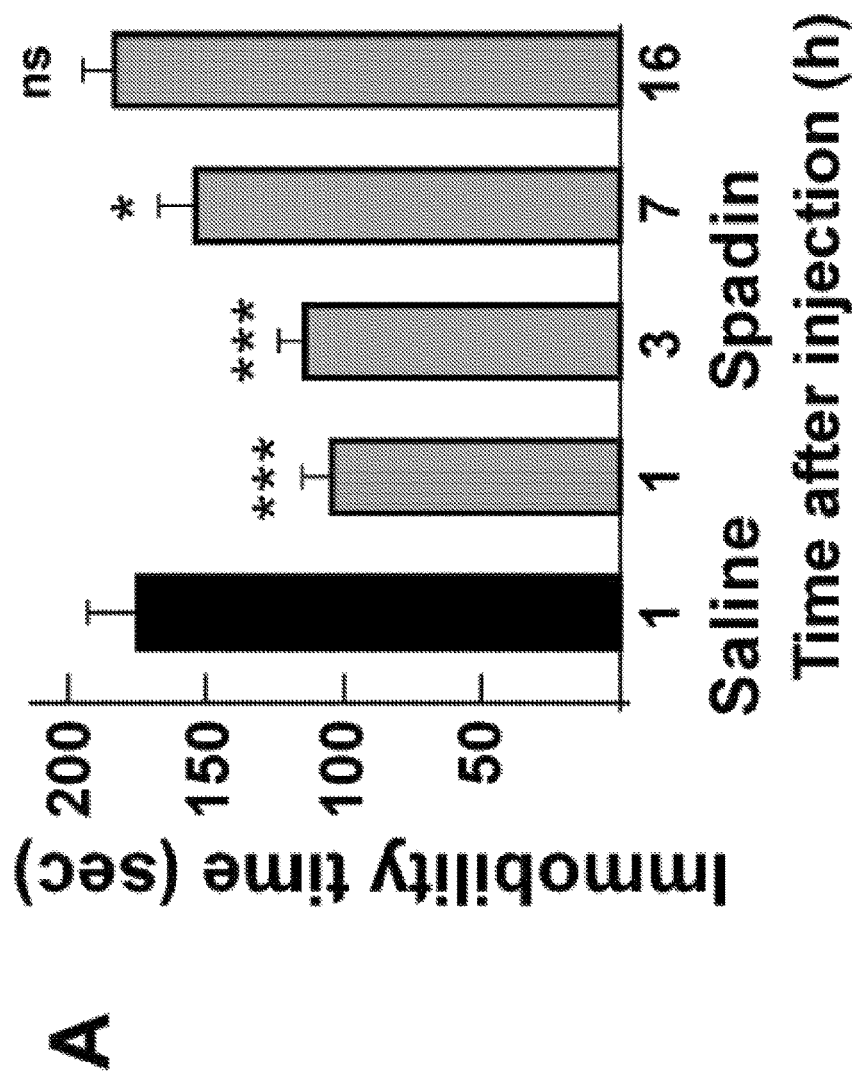
FIG. 4 are graphs showing the in vivo stability and/or duration of action of spadin and Analog 3 (SEQ ID:4) and Analog 8 (SEQ ID:9). Using the Forced Swimming Test (FST), comparing the in vivo duration of action of spadin (A) with both Analog 3 (SEQ ID NO:4) and Analog 8 (SEQ ID NO:9) (B).

Spadin was identified as a new antidepressant in rodent models. Spadin in vivo half-life measured by the FST was relatively short, around 7 hours (FIG. 4). TREK-1 was previously identified as the target for spadin in the depression process. With the aim to decrease the drug intake, spadin analogs were screened showing both an increased affinity for TREK-1 channels and an increased bioavailability compared to the native spadin counterpart.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents thereof.

What is claimed is:

1. A composition comprising at least one analog of spadin or at least one analog of a propeptide of spadin or mixtures thereof of said at least one analog, wherein said at least one analog is a retro-inverso peptide and is end-capped, and is selected from the group of: Ac-rlGwsvGipGswrplpa-NH$_2$ (SEQ ID NO:4), Ac-rlGwsvGi-NH$_2$ (SEQ ID NO:7), Ac-rlGwsvGipGswrplpaappppadlrdq-NH$_2$ (SEQ ID NO:9), Ac-rlGwsvGipGswrplpaappppa-NH$_2$ (SEQ ID NO:11), Ac-rrwrGGrpfaGGaaaarlGwsvGipGswrplpaappppadlrdq-NH$_2$ (SEQ ID NO:13), Ac-rlawsvaipaswrplpa-NH$_2$ (SEQ ID NO: 15), c(rlGwsvGipGswrplpa) (SEQ ID NO:20), c(rlGwsvGipGswrplparlGwsvGipGswrplpa) (SEQ ID NO:21) and mixtures thereof.

2. A method for blocking TREK-1 channel activity, said method comprising administering to an animal an effective amount of the pharmaceutical composition according to claim 1.

3. A pharmaceutical composition comprising, in a pharmaceutically acceptable vehicle, at least one analog of spadin or at least one analog of a propeptide of spadin or mixtures thereof of said at least one analog, wherein said at least one analog is a retro-inverso peptide and is end-capped, and is selected from the group of: Ac-rlGwsvGipGswrplpa-NH$_2$ (SEQ ID NO:4), Ac-rlGwsvGi-NH$_2$ (SEQ ID NO:7), Ac-rlGwsvGipGswrplpaappppadlrdq-NH$_2$ (SEQ ID NO:9), Ac-rlGwsvGipGswrplpaappppa-NH$_2$ (SEQ ID NO:11), Ac-rrwrGGrpfaGGaaaarlGwsvGipGswrplpaappppadlrdq-NH$_2$ (SEQ ID NO:13), Ac-rlawsvaipaswrplpa-NH$_2$ (SEQ ID NO: 15), c(rlGwsvGipGswrplpa) (SEQ ID NO:20), c(rlGwsvGipGswrplparlGwsvGipGswrplpa) (SEQ ID NO:21) and mixtures thereof.

4. A biodegradable pharmaceutical composition comprising at least one analog of spadin or at least one an analog of a propeptide of spadin or mixtures thereof of said at least one analog in a biodegradable slow release vehicle, wherein the at least one analog of spadin or the at least one analog of a propeptide of spadin or mixtures thereof of said at least one analog is a retro-inverso peptide and is end-caped, and is selected from the group of: Ac-rlGwsvGipGswrplpa-NH$_2$ (SEQ ID NO:4), Ac-rlGwsvGi-NH$_2$ (SEQ ID NO:7), Ac-rlGwsvGipGswrplpaappppadlrdq-NH$_2$ (SEQ ID NO:9), Ac-rlGwsvGipGswrplpaappppa-NH$_2$ (SEQ ID NO:11), Ac-rrwrGGrpfaGGaaaarlGwsvGipGswrplpaappppadlrdq-NH$_2$ (SEQ ID NO:13), Ac-rlawsvaipaswrplpa-NH$_2$ (SEQ ID NO: 15), c(rlGwsvGipGswrplpa) (SEQ ID NO:20), c(rlGwsvGipGswrplparlGwsvGipGswrplpa) (SEQ ID NO:21) and mixtures thereof.

5. A biodegradable pharmaceutical composition comprising Ac-rlGwsvGipGswrplpa-NH$_2$ (SEQ ID NO:4) or Ac-rlGwsvGipGswrplpaappppadlrdq-NH$_2$ (SEQ ID NO:9) or Ac-rlGwsvGipGswrplpa-NH$_2$ (SEQ ID NO:4) and Ac-rlG-wsvGipGswrplpaappppadlrdq-NH$_2$ (SEQ ID NO:9) in a biodegradable slow release vehicle.

\* \* \* \* \*